US010131915B2

(12) United States Patent
Roth et al.

(10) Patent No.: US 10,131,915 B2
(45) Date of Patent: Nov. 20, 2018

(54) INDEPENDENTLY INDUCIBLE SYSTEM OF GENE EXPRESSION

(71) Applicant: Rutgers, The State University of New Jersey, New Brunswick, NJ (US)

(72) Inventors: Monica Roth, New York, NY (US); William Schneider, Hamilton, NJ (US); Gaetano T. Montelione, Highland Park, NJ (US); Masayori Inouye, Highland Park, NJ (US); Yuefeng Tang, Highland Park, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 122 days.

(21) Appl. No.: 15/198,648

(22) Filed: Jun. 30, 2016

(65) Prior Publication Data

US 2017/0137831 A1   May 18, 2017

Related U.S. Application Data

(62) Division of application No. 13/122,547, filed as application No. PCT/US2009/059574 on Oct. 5, 2009.

(60) Provisional application No. 61/211,605, filed on Mar. 31, 2009, provisional application No. 61/195,139, filed on Oct. 4, 2008.

(51) Int. Cl.
| | |
|---|---|
| *C12N 15/72* | (2006.01) |
| *C12N 1/20* | (2006.01) |
| *C12N 15/63* | (2006.01) |
| *C12N 15/67* | (2006.01) |
| *C07K 14/31* | (2006.01) |
| *C12N 9/22* | (2006.01) |

(52) U.S. Cl.
CPC ............. *C12N 15/72* (2013.01); *C07K 14/31* (2013.01); *C12N 1/20* (2013.01); *C12N 9/22* (2013.01); *C12N 15/635* (2013.01); *C12N 15/67* (2013.01); *C12Y 301/00* (2013.01); *C07K 2319/02* (2013.01); *H05K 999/99* (2013.01)

(58) Field of Classification Search
None
See application file for complete search history.

(56) References Cited

U.S. PATENT DOCUMENTS 9,228,217 B2 * 1/2016 Montelione .............. C12N 9/22

FOREIGN PATENT DOCUMENTS

WO   2003074657 A2   9/2003
WO   2006055292 A2   5/2006

OTHER PUBLICATIONS

Mardanov et al. 2007 (Tightly regulated, high-level expression from controlled copy number vectors based on the replicon of temperate phage N15; Gene 395: 15-21) (Year: 2007).*
Suzuki et al. 2005 (Single Protein Production in Living Cells Facilitated by an mRNA Interferase; Molecular Cell 18:253-261) (Year: 2005).*
Saenger et al. 2000 (The Tetracycline Repressor—A paradigm for a biological switch; Angew. Chem. Int. Ed. 39: 2042-2052) (Year: 2000).*
Gardner et al. 2000 (Construction of a genetic toggle switch in *Escherichia coli*; Nature 403: 339-342). (Year: 2000).*
Qing et al. 2004 (Cold-shock induced high yield protein production in *Escherichia coli*; Nature Biotechnology 22(7): 877-882) (Year: 2004).*
Baneyx 1999 (Recombinant protein expression in *Escherichia coli*; Current Opinion in Biotechnology 10:411-421). (Year: 1999).*
Somerville 1988(The trp Promoter of *Escherichia coli* and its exploitation in the design of Efficient protein production systems; Biotechnology and Genetic Engineering Reviews 6: 1-42) (Year: 1988).*
Suzuki, et al: "Single Protein Production (SPP) System in *Escherichia coli*", Nature Protocols, 2007, vol. 2, No. 7, pp. 1802-1810.
Lutz et al: "Independent and Tight Regulation of Transcriptional Units in *Escherichia coli* via the LacR/O, the TetR/O and Arac/I1-12 Regulatory Elements", Nucleic Acids Research, 1997, vol. 25, No. 6, pp. 1203-1210.
Takahara, et al: "The ompA Signal peptide Directed Secretion of Staphylococcal Nuclease A by *Escherichia coli*", The Journal of Bilogical Chemistry, Mar. 10, 1985, vol. 260, No. 5, pp. 2670-2674.

* cited by examiner

*Primary Examiner* — Mary Maille Lyons
(74) *Attorney, Agent, or Firm* — Fox Rothschild LLP

(57) ABSTRACT

The present invention is directed to the improved methods for the temporal induction of proteins using the condensed single protein production (cSPP) system.

7 Claims, 16 Drawing Sheets

Specification includes a Sequence Listing.

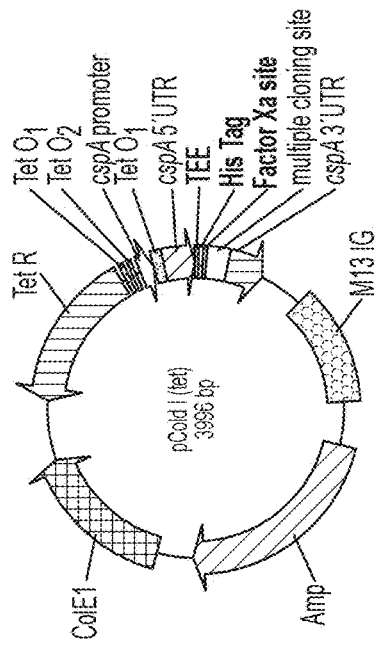
FIG. 1A
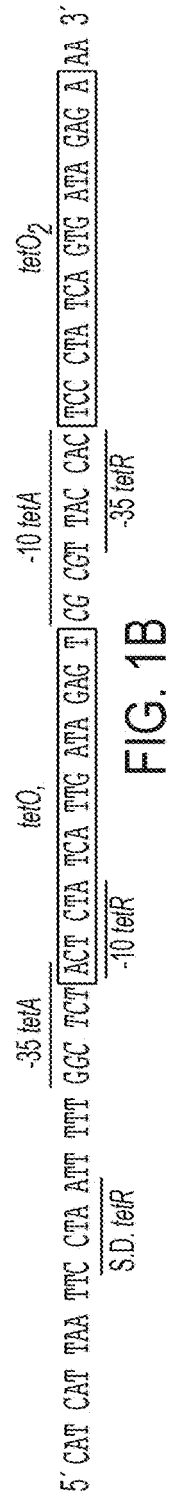
FIG. 1B
FIG. 1C

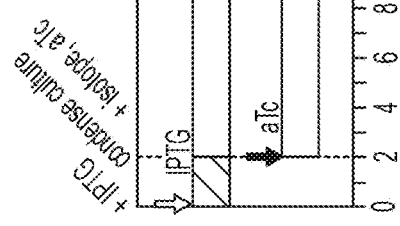
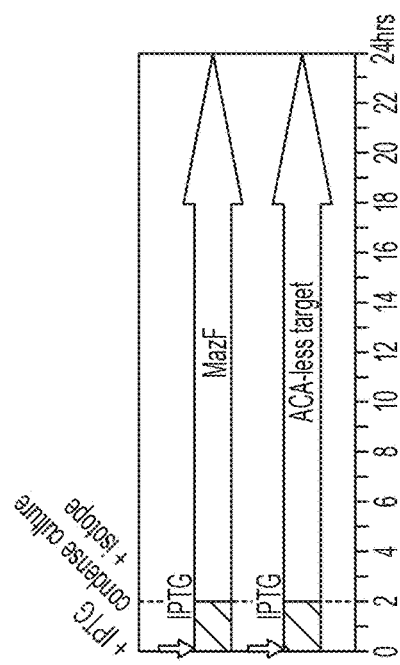
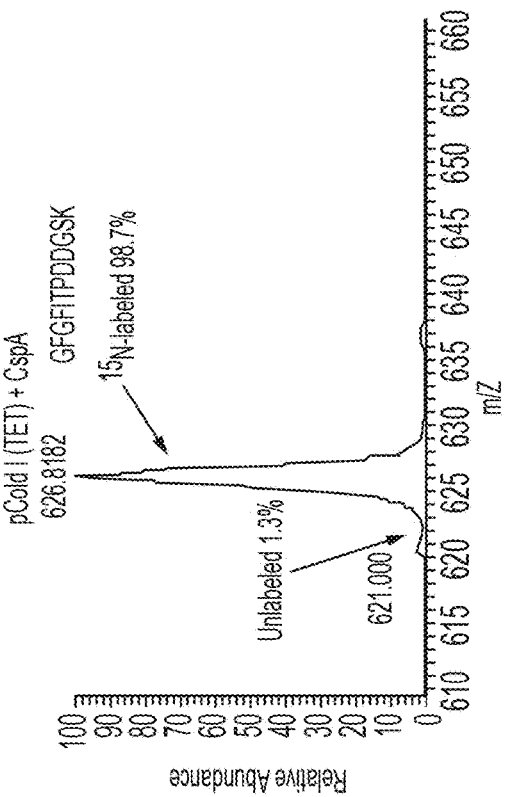
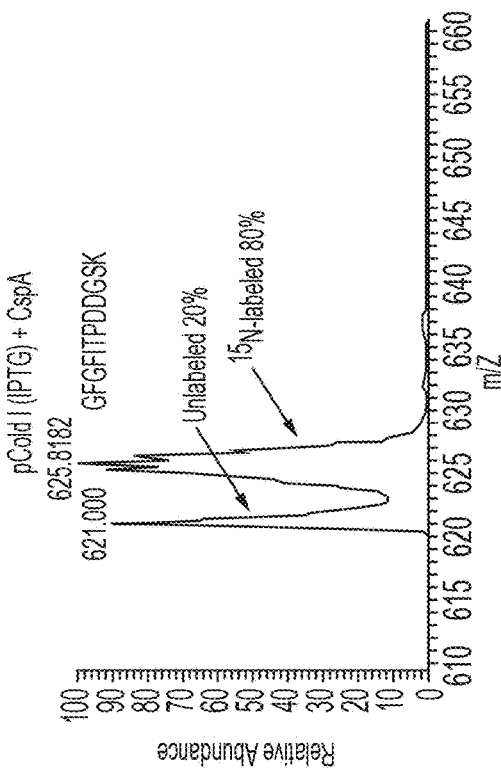

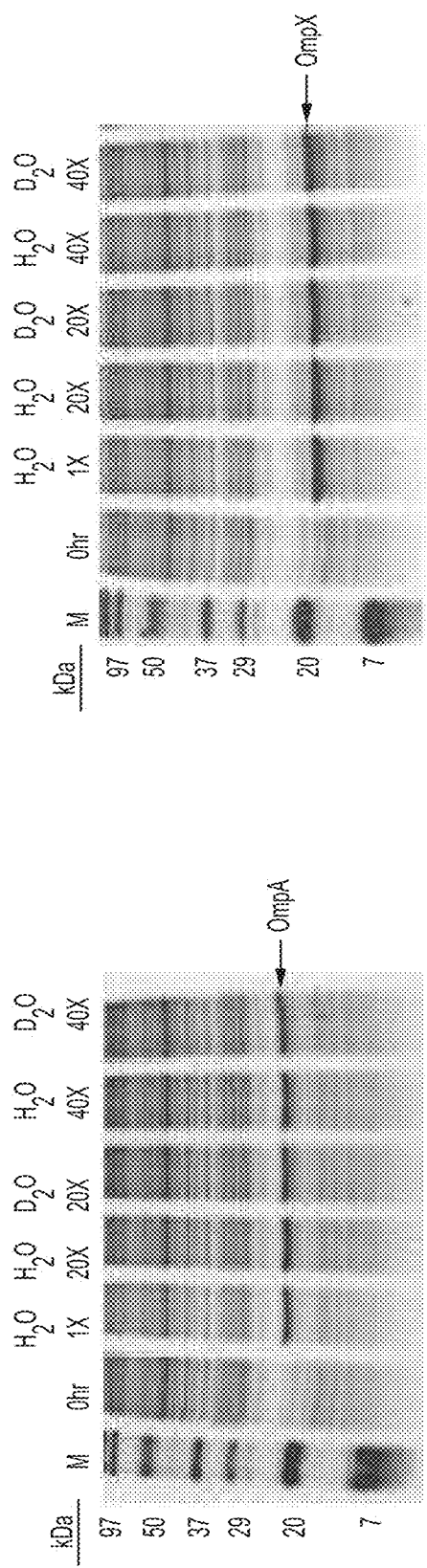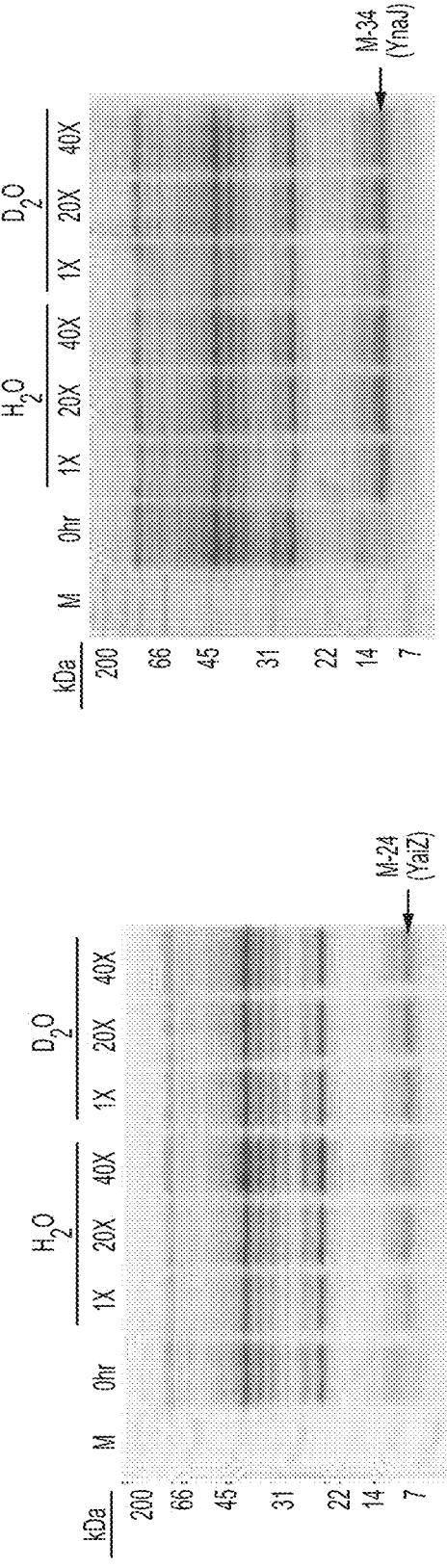
FIG. 5A
FIG. 5B
FIG. 5C
FIG. 5D

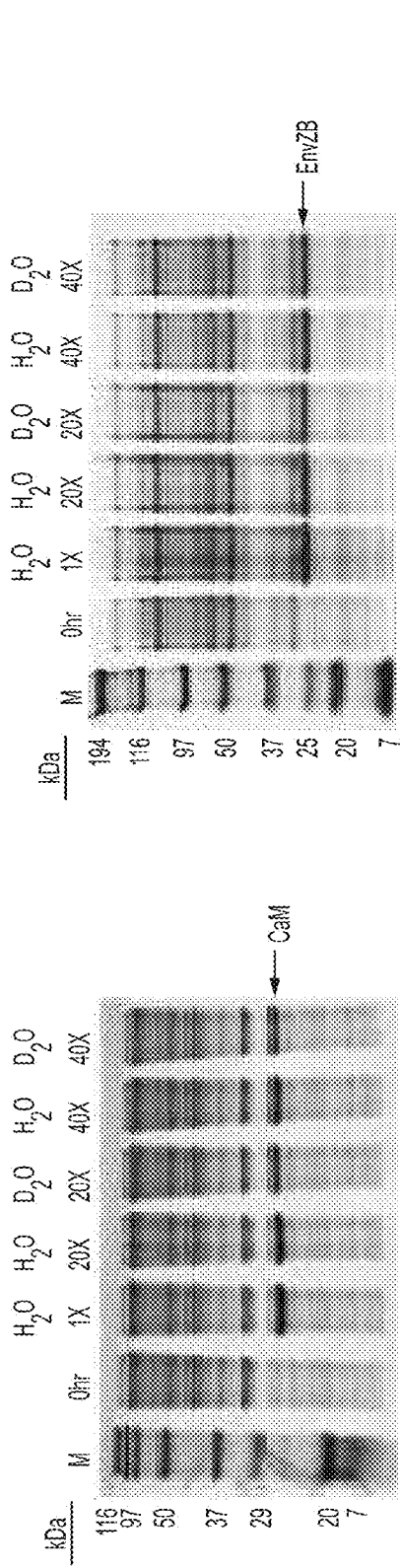
FIG. 5E
FIG. 5F
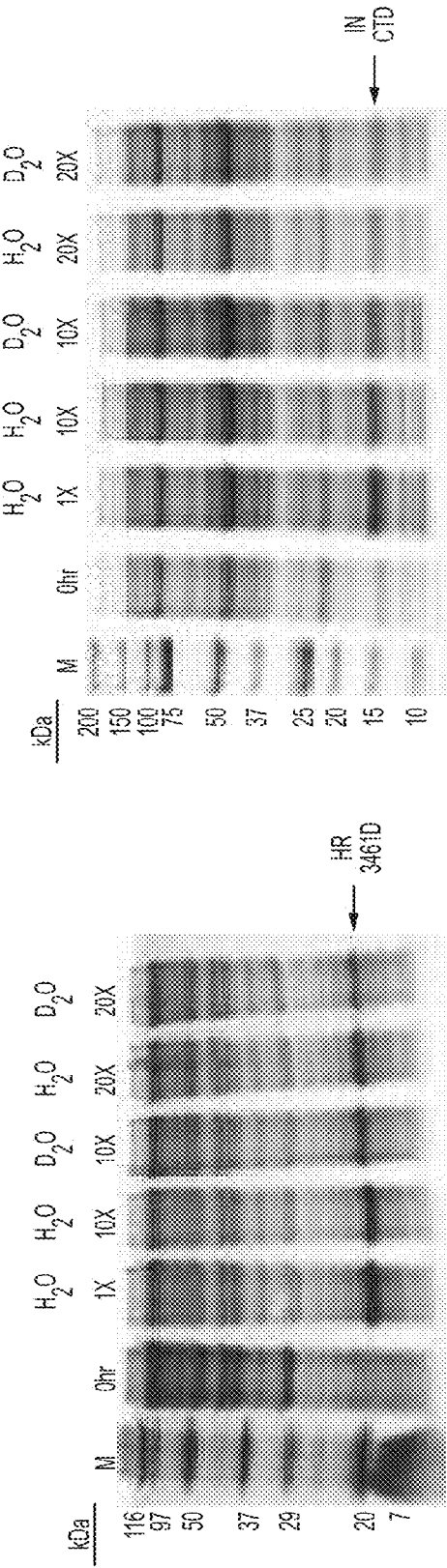
FIG. 5G
FIG. 5H

SEQUENCE LISTING

```
<160> NUMBER OF SEQ ID NOS: 13

<210> SEQ ID NO 1
<211> LENGTH: 17
<212> TYPE: PRT
<213> ORGANISM: Artificial Sequence
<220> FEATURE:
<223> OTHER INFORMATION: CspA trypsin fragment

<400> SEQUENCE: 1

Ser Leu Asp Glu Gly Gln Lys Val Ser Phe Thr Ile Glu Ser Gly Ala
1               5                   10                  15

Lys

<210> SEQ ID NO 2
<211> LENGTH: 14
<212> TYPE: PRT
<213> ORGANISM: Artificial Sequence
<220> FEATURE:
<223> OTHER INFORMATION: EnvZB trypsin fragment

<400> SEQUENCE: 2

Thr Ile Ser Gly Thr Gly Leu Gly Leu Ala Ile Val Gln Arg
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Tryptic fragment of the M-MLV Integrase
      N-terminal domain
<220> FEATURE:
<221> NAME/KEY: UNSURE
<222> LOCATION: (7)..(7)
<223> OTHER INFORMATION: Oxidation at residue 7

<400> SEQUENCE: 3

Ser His Ser Pro Tyr Tyr Met Leu Asn Arg
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Tag sequence
<220> FEATURE:
<221> NAME/KEY: UNSURE
<222> LOCATION: (15)..(16)
<223> OTHER INFORMATION: Protease cleavage site between residues 15 and
      16

<400> SEQUENCE: 4

Met Asn His Lys Val His His His His His His Ile Glu Gly Arg His
1               5                   10                  15

Met
```

<210> SEQ ID NO 5
<211> LENGTH: 12
<212> TYPE: PRT
<213> ORGANISM: Artificial Sequence
<220> FEATURE:
<223> OTHER INFORMATION: Tag sequence

<400> SEQUENCE: 5

Met Asn His Lys Val His His His His His His Met
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Tag sequence

<400> SEQUENCE: 6

Met Asn His Lys Val His Met
1               5

<210> SEQ ID NO 7
<211> LENGTH: 11
<212> TYPE: PRT
<213> ORGANISM: Artificial Sequence
<220> FEATURE:
<223> OTHER INFORMATION: Tag sequence

<400> SEQUENCE: 7

Met Gly His His His His His His Ser His Met
1               5                   10

<210> SEQ ID NO 8
<211> LENGTH: 24
<212> TYPE: PRT
<213> ORGANISM: Artificial Sequence
<220> FEATURE:
<223> OTHER INFORMATION: Tag sequence
<220> FEATURE:
<221> NAME/KEY: UNSURE
<222> LOCATION: (21)..(22)
<223> OTHER INFORMATION: Protease cleavage site between residues 21 and
      22

<400> SEQUENCE: 8

Met Asn His Lys Val His His His His His Ser Ser Gly Arg Glu
1               5                   10                  15

Asn Leu Tyr Phe Gln Gly His Met
            20

<210> SEQ ID NO 9
<211> LENGTH: 23
<212> TYPE: PRT
<213> ORGANISM: Artificial Sequence
<220> FEATURE:
<223> OTHER INFORMATION: Tag sequence
<220> FEATURE:
<221> NAME/KEY: UNSURE
<222> LOCATION: (21)..(22)
<223> OTHER INFORMATION: Protease cleavage site between residues 21 and
      22

```
<400> SEQUENCE: 9

Met Lys Lys Thr Ala Ile Ala Ile Ala Val Ala Leu Ala Gly Phe Ala
1               5                   10                  15

Thr Val Ala Gln Ala His Met
            20

<210> SEQ ID NO 10
<211> LENGTH: 28
<212> TYPE: PRT
<213> ORGANISM: Artificial Sequence
<220> FEATURE:
<223> OTHER INFORMATION: Tag sequence
<220> FEATURE:
<221> NAME/KEY: UNSURE
<222> LOCATION: (21)..(22)
<223> OTHER INFORMATION: Protease cleavage site between residues 21 and
      22

<400> SEQUENCE: 10

Met Lys Lys Thr Ala Ile Ala Ile Ala Val Ala Leu Ala Gly Phe Ala
1               5                   10                  15

Thr Val Ala Gln Ala His His His His His His Met
            20                  25

<210> SEQ ID NO 11
<211> LENGTH: 12
<212> TYPE: PRT
<213> ORGANISM: Artificial Sequence
<220> FEATURE:
<223> OTHER INFORMATION: Tryptic fragment of CspA

<400> SEQUENCE: 11

Gly Phe Gly Phe Ile Thr Pro Asp Asp Gly Ser Lys
1               5                   10

<210> SEQ ID NO 12
<211> LENGTH: 5
<212> TYPE: PRT
<213> ORGANISM: Artificial Sequence
<220> FEATURE:
<223> OTHER INFORMATION: Translational enhancing element

<400> SEQUENCE: 12

Met Asn His Lys Val
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic

<400> SEQUENCE: 13

His His His His His His
1               5
```

US 10,131,915 B2

INDEPENDENTLY INDUCIBLE SYSTEM OF GENE EXPRESSION

This application claims priority to U.S. Provisional Application Ser. No. 61/195,139 filed Oct. 4, 2008 and 61/211,605 filed Mar. 31, 2009, the disclosures of which are hereby incorporated by reference in their entireties.

BACKGROUND OF THE INVENTION

The production of high quality isotope-enriched protein samples is a prerequisite for applying modem NMR methods for protein structure determination. Although NMR spectroscopy is well suited for rapid semi-automated structure determination of small proteins (MW<15 kDa), solving structures of larger proteins and multimeric complexes is considerably more challenging. As the size of the molecule increases, so does the molecule's rotational correlation time and, consequently, the efficiency of $^1$H—$^1$H relaxation mechanisms. One way to suppress these effects is to incorporate deuterium into the protein sample, diluting the $^1$H—$^1$H relaxation networks and increasing $^{13}$C and $^{15}$N relaxation times, resulting in sharper line widths for $^{13}$C, $^{15}$N and remaining $^1$H nuclei, and dramatically improved signal-to-noise ratios. Perdeuteration is generally required for studies of larger proteins, particularly membrane proteins. $^2$H, $^{13}$C,$^{15}$N-enriched protein samples are also central to certain strategies for fully automated analysis of small protein structures.

While deuterium incorporation into protein samples can greatly improve the quality of data collected, the sample preparation itself can be challenging. Cell growth is affected by increasing $^2$H$_2$O concentration, and cells must be gradually acclimated to high $^2$H$_2$O concentration in incremental steps. Once acclimated, additional isotopically-enriched reagents are introduced, and protein expression can proceed. However, the overall protein yield in these conditions is often significantly reduced. As fermentation media costs for production of uniformly $^2$H,$^{13}$C,$^{15}$N-enriched samples range from $1500-$3,000 per liter, or higher, perdeuteration methods are generally employed only when absolutely required; for this reason, many potential applications of perdeuterated samples in routine protein NMR applications have not been pursued.

Additionally, expression of the target gene prior to culture condensation and resuspension in isotope enriched medium leads to heterogeneously labeled protein and results in the accumulation of approximately 10-20% of the total protein completely unlabeled.

Thus there remains a need for a process that is more cost effective, and results in a higher percentage of labeled protein.

SUMMARY OF THE INVENTION

The inventors of the present application have developed a method for efficient production of perdeuterated, $^{13}$C-, $^{15}$N-enriched protein samples at a fraction of the cost of standard techniques.

To that end, in certain embodiments the present invention is directed to a vector comprising a cspA cold shock promoter; a tetR gene; a tet operator; and a gene encoding a target protein under the control of the tet operator.

In other embodiments, the present invention is directed to a cell containing a vector comprising a gene encoding a target protein; and a vector comprising a gene encoding an mRNA specific endoribonuclease, wherein the target protein and mRNA-specific endoribonuclease are capable of being induced with different substances.

In yet other embodiment, the invention is directed to a method of labeling a target protein comprising contacting a culture of cells containing the vectors described herein with a substance capable of inducing the mRNA-specific endoribonuclease; and contacting a culture of the cells with an isotope-enriched medium comprising a substance capable of inducing the target protein. In preferred embodiments, the present invention provides for labeling of at least 85%, at least 90% or at least 95% of the target protein.

Other embodiments of the present invention are directed to a protein labeled by the methods described herein.

Other features and advantages of the invention will be apparent from the following description of the preferred embodiments thereof, and from the claims.

BRIEF DESCRIPTION OF THE FIGURES

FIGS. 1A, 1B and 1C depict a pColdI(tet) vector map;

FIGS. 4A, 4B, 4C and 4D depict an isotope incorporation in the co-inducible vs. dual inducible eSPP systems wherein Panels A and B presents a schematic of the isotope incorporation between (A) the co-inducible pCold(IPTG) vectors, and (B) the dual inducible pCold(tet) vectors. Grey shading indicates protein produced in unlabeled medium; blue arrows indicate time of IPTG induction; black arrow indicates time of anhydrotetracycline (aTe) induction. Panels C and D depict representative trypsin fragment of CspA protein expressed at 40× condensation in $^{15}$N-labeled minimal medium. Predicted weight of unlabeled and fully labeled, double charged peptide is 621.00 and 626.70 Daltons, respectively;

FIGS. 5A, 5B, 5C, 5D, 5E, 5F, 5G, 5H, 5I and 5J depict a SDS-PAGE analysis of various proteins expressed in condensed-phase SPP system, comparing expression in H$_2$O and $^2$H$_2$O (a-j). The names of each protein, degree of condensation, and solvent (H$_2$O or $^2$H$_2$O) are indicated in each panel. Panels a-d illustrate 4 E. coli membrane proteins expressed using the cSPP(IPTG) system. Panel a, OmpA; panel b, OmpX; panel c, YaiZ, panel d, YnaJ. Panels e-f illustrate two soluble proteins expressed using the cSPP (IPTG) system. Panel e, calomodulin (CaM), (eukaryotic); panel f, EnvZB (E. coli). Panels g-j illustrates four additional eukaryotic (HR 3461D) and viral (El B19K, CTD, NTD) proteins expressed with the cSPP(tet) system. Panel g, domain of human proto-oncogene tyrosine protein kinase FER, residues 453-557 (HR3461D); panel h, C-terminal domain of murine leukemia virus integrase, residues 287-381 (IN CTD); panel i, adenovirus El B19K; panel j, N-terminal domain of murine leukemia virus integrase, residues 9-105 (IN NTD);

DETAILED DESCRIPTION

Figure 2:
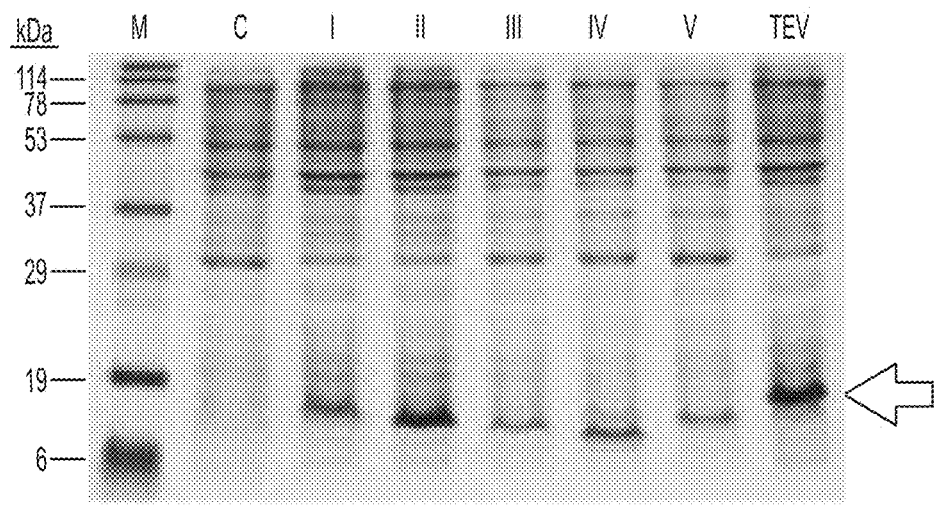
FIG. 2 depicts the expression of a truncated C-terminal domain from M-MuLV IN in the full panel of pCold(tet) vectors wherein M, protein marker; C, negative control (pColdIV(tet), no aTc induction); I, pColdI(tet); II, pColdII (tet); III, pColdIII(tet); IV, pColdIV(tet); X, pColdX(tet); TEV, pColdTEV(tet)

The inventors of the present application have discovered that by optimizing the previously described condensed single protein production (eSPP) method of protein production in *E. coli*, high levels of specific proteins can be produced in deuterium-based, isotope-enriched minimal medium.

The cSPP method utilizes a bacterial toxin, the endoribonuclease MazF that specifically cleaves mRNAs at ACA sequences, forcing the cells into a semi-dormant state. By engineering a target gene to be devoid of ACA sequences, and therefore resistant to MazF cleavage, it is possible to not only selectively express and isotope-enrich a targeted protein, but to do so in a dramatically reduced (condensed) culture volume. In this work, it was discovered that the cSPP method requires no acclimation steps for protein expression in deuterated media, and allows as much as 40-fold (or higher) condensation of the culture prior to induction of target protein expression with no significant reduction in protein yield per cell. Using such perdeuterated samples of the E. coli cold shock protein A (CspA), rapid (~3.5 day) NMR data collection, fully automated analysis of resonance assignments, and high quality 3D structure determination without the need for side chain resonance assignments using the CS-Rosetta method were demonstrated. The combined methods of inexpensive perdeuteration and CS-Rosetta, provide the basis for a high-throughput approach for routine, rapid, high-quality structure determination of small proteins.

Also, the cSPP system can be used for cost-effective production of $^2H$, $^{13}C$, $^{15}N$-enriched membrane proteins, including E. coli plasma membrane protein YaiZ and outer membrane protein X (OmpX). Protein perdeuteration approaches have tremendous value in protein NMR studies, but are limited by the high cost of perdeuterated media. However, it has been discovered that the condensed Single Protein Production (cSPP) method can be used to provide high-quality $^2H$, $^{13}C$, $^{15}N$-enriched protein samples at 2.5-10% the cost of traditional methods. As an example of the value of such inexpensively-produced perdeuterated proteins, $^2H$, $^{13}C$, $^{15}N$-enriched E. coli cold shock protein A (CspA) were produced in 40× condensed phase media, and a high-accuracy 3D structure using CS-Rosetta was determined. The cSPP system was also used to produce, $^2H$, $^{13}C$, $^{15}N$-enriched E. coli plasma membrane protein YaiZ and outer membrane protein X (OmpX) in condensed phase. NMR spectra can be obtained for these membrane proteins following simple detergent extraction, without extensive purification or reconstitution, allowing a membrane protein's structural and functional properties to be characterized prior to reconstitution, or as a probe of the effects of subsequent purification steps on the structural integrity of membrane proteins. The 10-40 fold reduction in costs of fermentation media provided by using the cSPP system opens the door to many new applications for perdeuterated proteins in spectroscopic and crystallographic studies.

One weakness of the available set of cSPP vectors, however, was the accumulation of unlabeled protein due to expression prior to culture condensation. Specifically, although the previously described cSPP system allowed for protein production and isotope enrichment at a fraction of the cost incurred with traditional methods, a substantial amount (10-20%) of the target protein remained unlabeled due to the co-induction of the target protein for 2 hr with the MazF toxin upon addition of IPTG and prior to culture condensation. While in many NMR applications such as $^1H$—$^{15}N$ detected triple resonance experiments, this unenriched population of protein is not visible, it contributes effectively to lowering the yield of isotope-enriched species and reducing the effective signal-to-noise of the NMR experiment. These unenriched species in the NMR sample can also create artifacts and complicate interpretation of X-filtered NMR experiments.

It has now been found that in order to remedy this problem, the induction of the target protein can be temporally regulated by placing the pCold vectors under control of the tet $O_1$ operator. A toolbox of vectors has been developed herein for expression in the cSPP system where temporal regulation of the ACA-less target gene results in greater than 95% isotope enrichment and a reduction in isotopic heterogeneity. This has direct applications to protein NMR for structural genomics and structural biology studies, specifically in applications requiring the production of isotope-enriched proteins.

By temporally separating the induction of the MazF toxin from that of the target protein it is now possible to nearly eliminate contamination from the unlabeled target protein and obtain a protein product that is much more homogeneous with respect to isotopic-enrichment. This is critical for certain applications in which labeled species A is mixed with unlabeled species B, and NMR is used to detect interactions between species A and species B as an interaction between a labeled and an unlabeled species; this application fails if, for example, there is a significant component of unlabeled molecules in the sample of labeled species A. In addition to the series of pCold(tet) vectors in the table below, two additional pCold(tet) vectors have been constructed. pColdVb(tet) and pColdVbHis(tet) encode an N-terminal fusion tag comprising the OmpA signal peptide resulting in peptide secretion. The signal peptide is cleaved by a cellular protease (signal peptidase 1) during secretion. pColdVbHis(tet) additionally encodes a $His_6$ fusion tag, that remains post protease cleavage.

Similar to the pCold(tet) vectors in the table below, the pColdVb(tet) and pColdVbHis(tet) vectors drive target gene expression from the cspA promoter and are regulated by the $tetO_1$ operator.

TABLE 1 highlights the various features of the pCold(tet) vectors

| Vector | TEE | His Tag | Tag sequence | Protease | kDa tag |
|---|---|---|---|---|---|
| pColdI(tet) | + | + | MNHKVHHHHHHIEGR/HM (SEQ ID NO: 4) | Factor Xa | 2.04 kDa |
| pColdII(tet) | + | + | MNHKVHHHHHM (SEQ ID NO: 5) | — | 1.45 kDa |
| pColdIII(tet) | + | - | MNGKVHM (SEQ ID NO: 6) | — | 0.76 kDa |
| pColdIV(tet) | - | - | — | — | — |
| pColdX(tet) | - | + | MGHHHHHHSHM (SEQ ID NO: 7) | — | 1.25 kDa |
| pColdTEV(tet) | + | + | MNHKVHHHHHHSSGRENLYFQ/GHM (SEQ ID NO: 8) | TEV | 2.83 kDa |
| pColdVb(tet) | - | - | MKKTAIAIAVALAGFATVAQNHM (SEQ ID NO: 9) | Cellular | 2.31 kDa |

TABLE 1-continued highlights the various features of the pCold(tet) vectors

| Vector | TEE | His Tag | Tag sequence | Protease | kDa tag |
|---|---|---|---|---|---|
| pColdVbHis(tet) | - | + | MKKTAIAIAVALAGFATVAQA/HHHHHHM (SEQ ID NO: 10) | Cellular | 3.00kDa |

Using this set of vectors, it is now possible to test several different constructs for optimal protein expression in the cSPP(tet) system. The results presented below show two proteins, one bacterial (CspA) that can be condensed 40×, and one viral (M-MuLV IN C-terminal domain) that can be condensed 10×. Additional experiments have allowed the N-terminal Zn binding domain of M-MuLV IN to be similarly expressed, condensed 15×, and selectively labeled with amino acid precursors. Thus the generality of this vectors system is firmly established.

It is important to note that tetracycline addition is toxic to bacteria at concentrations at or higher than 0.5 μg/ml. In order to maximize induction of the target proteins, modified tetracycline derivatives are utilized, which display lower toxicity and thus can be present in higher concentrations (e.g. anhydrotetracycline, 2 μg/ml). In the SPP system described herein, to achieve maximal induction of target gene expression of uncondensed cultures, concentrations of tetracycline approaching the toxicity limit are required. For this reason anhydrotetracycline is utilized at a concentration of 0.2 μg/mL. When the cell culture is condensed to greater densities the concentration of anhydrotetracycline must also be increased in a linear fashion to compensate for the increased cell number and active transport of anhydrotetracycline across the cell membrane. Generally, the degree of condensation is multiplied by 0.15 μg/mL of anhydrotetracycline to give the final concentration of drug required for optimal induction. In this respect a 1× (uncondensed) culture is induced at 0.2 μg/mL of anhydrotetracycline while a 10× culture would be induced at 1.5 μg/mL, and similarly a 40× culture would be induced at a final concentration of 6.0 μg/mL of anhydrotetracycline. It should be noted that in this fashion the known toxicity limit for anhydrotetracycline of 2.0 μg/mL can be exceeded with no toxic effects.

The maintenance of MazF under the IPTG induction and placing the target protein under tetracycline analog regulation also limits the toxicity associated with tetracycline because the variability resulting from inducing MazF under tetracycline is eliminated, which creates additional stress to cells. Thus, under condensed cell cultures, the toxicity limit of anhydrous Tet can exceed the reported levels. This maximizes the induction levels of the target proteins.

While it has been effectively shown that a tetracycline based approach to gene expression control has been successful, the dual induction approach is not limited to tetracycline and alternative induction methods can similarly be used.

Replacing the tet repressor gene, tetR, in the pCold(tet) vectors with the trp repressor gene, trpR, and likewise replacing the tet operator, tet $O_1$, with the trp operator sequence would allow for target gene induction upon addition of the inducer, 3-β-indoleacrylic acid (IAA).

Additional examples of dual inducible systems for use in cSPP include regulating MazF expression with L-arabinose induction by introducing the $O_1$ and $O_2$ operator and $I_1$ and $I_2$ initiation regions upstream of mazF and including the transcription regulator araC gene on the plasmid. This would provide similar induction conditions to that of the pBAD vector series, allowing for target gene induction to be temporally regulated with either of the IPTG or tetracycline inducible versions of the pCold plasmids currently available.

Similar to regulating the mazF gene by L-arabinose induction, the previously described pRHA vector utilizing L-rhamnose for induction would have the added benefit of allowing for "titratable" levels of MazF production. This added feature would allow for various other combinations of target gene induction, including pET vectors, as the amount of MazF produced at higher temperatures could be more tightly regulated. Using an all or none induction system, such as the lac operon, can be problematic when expressing MazF at the higher temperatures required for efficient target protein production in conventional expression systems such as pET, as MazF itself becomes toxic to the cells when expressed at high levels. The ability to titrate MazF production would open the door to various additional combinations of dual inducible scenarios.

In theory, any possible combination of inducible systems for protein production, including regulation by IPTG, tetracycline (e.g., anhydrotetracycline or alternatively with various other tetracycline analogues (for example, epi-anhydrocholoro-tetracylcine), L-arabinose, and L-rhamnose could be used to create a set of plasmids suitable for use in the dual inducible cSPP system.

Figure 3A:
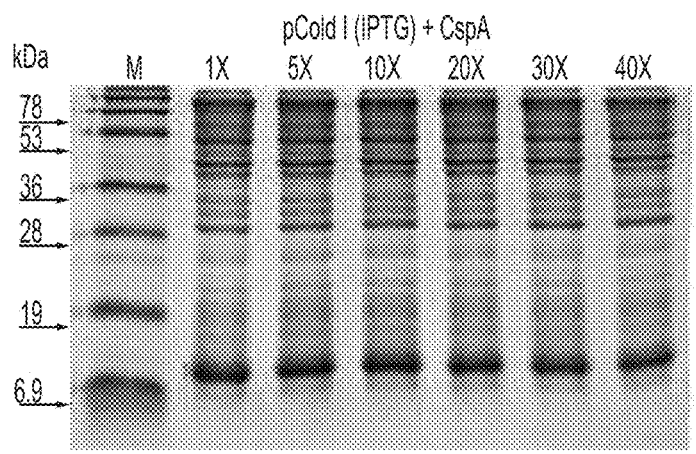
FIGS. 3A and 3B depict a comparison of protein expression and condensation of pColdI(IPTG) and pColdI(tet) wherein cultures expressing E. coli protein CspA were condensed 5×, 10×, 20×, 30×, 40×, and compared to uncondensed (1×) cultures in the (A), IPTG inducible pColdI (IPTG), and (B), tetracycline inducible pColdI(tet) vectors.
Figure 3B:
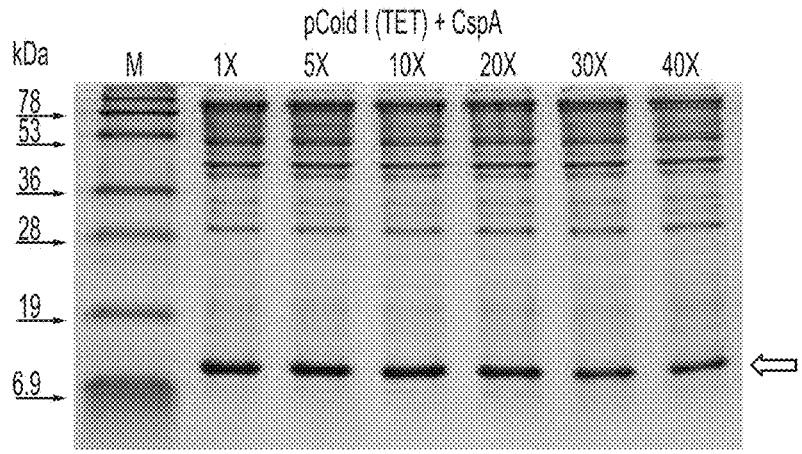
Figures 5I, 5J:
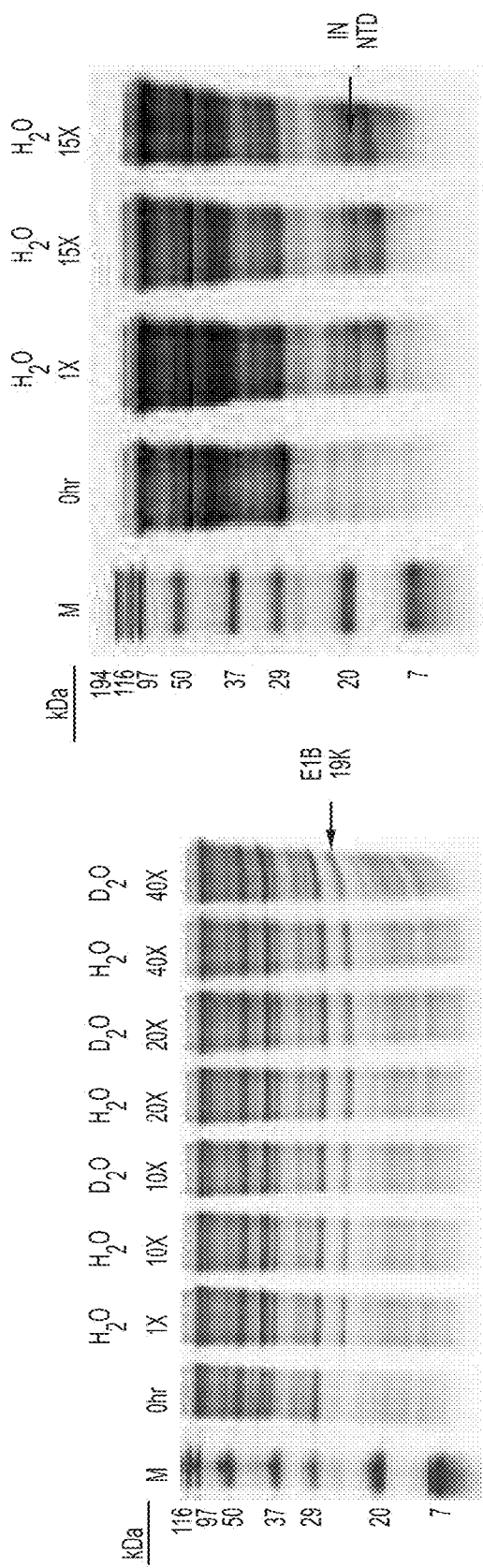

An embodiment of the dual induction system has been developed and verified with three independent bacterial (CspA) and viral proteins (MuLV Integrase N-terminal domain, Adenovirus ElB19K). Representative examples of protein expression levels at varying degrees of condensation with the described tetracycline inducible SPP system as compared to that of the established co-inducible SPP system are shown in FIGS. 3 and 5. Also shown in FIG. 4 are comparisons of $^{15}$N-isotope incorporation into the bacterial target protein CspA as measured by mass spectrometry of representative trypsin fragments.

The dual induction system has direct applications to systems requiring the high efficiency incorporation of labels into target protein. Under the previous system, target proteins are co-induced with MazF. One major benefit of the SPP system is that upon MazF induction and host protein shut down, the bacterial cells can be condensed and grown in a small volume. With the single induction system, the target proteins will still be expressed prior to the host-protein shut-down and condensation. The use of the condensed system allows for minimal use of label, tracer elements, and modified amino acids. By separating the induction systems, the cultures can be condensed prior to the addition of the tracer elements and prior to the separate induction of the target proteins. Thus the target protein will only be expressed in the presence of the labels.

The invention of an independently inducible single protein production (SPP) system greatly improves the quantity and quality of isotope labeled product for nuclear magnetic resonance (NMR) applications as well as various other practices requiring specifically labeled protein products as compared to the existing co-inducible SPP system.

Direct examples are the use in NMR structural studies. Structural studies of large proteins, often require the incorporation of $^2H_2O$, $^{15}N$ and $^{13}C$ labels. Using the single IPTG induction system, isotope-labeled markers were at best incorporated to 80% efficiency due to the three hour period of co-induction with MazF. This efficiency has increased to over 97% using the dual induction system, as judged by mass spectrometry of multiple isolated peptides. Thus, a reproducible high efficiency method of incorporating label specifically into the targeted protein has been developed. Alternative labels can use specific amino acids.

An additional application possible with the advent of the dual inducible cSPP system, not feasible with the co-inducible cSPP system is the production of asymmetrically labeled samples for NMR spectroscopy. Characterizing oligomer interface interactions can be challenging when determining protein structures by NMR as it is difficult to distinguish inter- from intra-molecular interactions. By producing an asymmetrically labeled protein sample, where one subunit in the complex is labeled differently from that of the other(s), it is possible to distinguish inter- from intra-molecular contacts.

Asymmetrically labeled samples such as those described for protein interface interactions above require that little to no unlabeled protein be present in the final sample. One strategy is to uniformly label the target protein with deuterium while supplying protonated forms of the compounds of interest. Two separate cultures could be prepared where one would produce protein specifically protonated at the amino acids ILV and the other would produce protein specifically protonated at the amino acids FYW. The cultures would then be combined in the purification process only after protein expression was complete in order to generate a mixed multimer. Assuming complete mixing, a ratio of 1:2:1 of mixed multimers would be expected, where 50% of the total protein contains an asymmetric interface. As the co-inducible cSPP system generates a high level of background, which would in this case be protonated, the above described experiment would not be feasible. The dual inducible cSPP system, by reducing the background protein expression prior to isotope enrichment, opens the door to this approach and similar approaches that require minimal to no background of unlabeled protein present.

Combining dual induction with the already established cSPP system offers the benefit of increased yield of isotope enriched protein and a significantly improved signal to noise ratios in NMR studies. The dual inducible cSPP(tet) system extends the established cSPP system to various applications such as 2D NMR on perdeuterated proteins and other systems that would not be possible using the co-induced cSPP system. The condensability of the culture using these systems opens the door to many applications in structural and functional genomics in which high protein yields are required in small sample volumes, including microtiter plate fermentation methods. It is expected that the dual inducible expression systems described here, allowing condensation of 10-40 fold in fermentations for isotopic-enrichment, will become the default systems used for producing isotope-enriched proteins in *E. coli* for NMR, mass spectrometry, neutron diffraction, and a wide range of other applications in molecular biophysics and biotechnology.

EXAMPLES

Example 1

Materials and Methods
Vector Cloning.

The complete sequences of the pCold(tet) vectors including pColdI(tet), pColdII(tet), pColdIII(tet), pColdIV(tet), pColdX(tet), and pColdTEV(tet), have been deposited in Genbank. Beginning with pColdI(SP-4) as the parental vector pColdI(tet) was generated in the following manner: The lacI gene and upstream region, up to but not including the cspA promoter, was replaced with the tetR gene and a modified version of the promoter-operator region of tetA and tetR from Tn10. The tetA and tetR promoter-operator region was cloned upstream of the existing cspA cold shock promoter in order to avoid disrupting transcription of the target gene by the cold shock promoter. In addition, the DNA sequence of the lac operator region within the 5'UTR of cspA controlling induction of the target gene was mutated to that of the tet operator $tetO_1$ The Tn10 promoter-operator region consists of two tet repressor binding sites, $tetO_1$ and $tetO_2$ with overlapping promoters driving transcription in opposite directions. Only transcription of the tetR gene was required therefore the −10 and −35 elements of the tetA promoter were mutated to avoid potential interference with the adjacent cspA promoter driving target gene expression. Generation of pCold II, III, and IV(tet) vectors proceeded by cloning the region upstream of the multiple cloning site between NheI and NdeI, containing the various fusion tag sequences from the pCold series into the pColdI(tet) backbone. pColdX(tet) and pColdTEV(tet) inserts were generated by synthesizing the appropriate fusion tag sequences via overlapping PCR and cloning the resulting DNA product into the pColdI(tet) vector between NheI and NdeI.

An ACA-less cspA gene, as previously described in Suzuki, M et al (2005) "Single protein production in living cells facilitated by an mRNA interferase." Mol Cell 18, 253-261, incorporated herein by reference in its entirety, was sub-cloned into the pColdI(tet) vector between the NdeI and BamHI restriction sites for protein expression. A truncated C-terminal ACA-less gene construct from Thr287-Gly381 of the Moloney Murine Leukemia Virus (M-MuLV) Integrase (IN) protein was codon optimized for *E. coli* and synthesized by overlapping PCR. The resulting DNA product was then sub-cloned into the Nde I and BamH I restriction sites of the pCold(tet) series of vectors for protein expression.

Protein Expression.

pCold(tet) vectors containing the desired insert were transformed into chemically competent BL21(DE3) cells containing the vector pACYCmazF, as previously described in Suzuki, M. et al. (2007) "Single protein production (SPP) system in *Escherichia coli*" Nat Protoc 2, 1802-1810, incorporated herein by reference in its entirety. Single colonies were picked and inoculated into 2 ml of M9CAA containing 30 µg/ml chloramphenicol for selection of pACYCmazF and 100 µg/ml carbenicillin for selection of pCold(tet), and grown overnight (20 hr). The following day, M9 medium containing 30 µg/ml chloramphenicol and 100 µg/ml carbenicillin was inoculated at 5 µl/ml and grown overnight (20 hr). Fresh M9 medium containing 30 µl/ml chloramphenicol and 100 µg/ml carbenicillin was then inoculated at 10% with the overnight culture and grown at 37° C. until the $OD_{600}=0.5$ and then the cultures were rapidly cooled while swirling in an ice bath for 10-15 min. The MazF protein was induced with 1 mM IPTG and cultures were incubated at 15°

C. for an additional 2 hr while shaking. Cell cultures are then centrifuged for 10 min at 4° C. at 5000×g and resuspended in the desired condensed culture volume of M9 medium or $^{15}$N-enriched M9 medium (in which $^{15}$NH$_4$Cl is the sole source of nitrogen) containing 30 µg/ml chloramphenicol, 100 µg/ml carbenicillin, 1 mM IPTG, and anhydrotetracycline. The level of anhydrotetracycline varied with the level of condensation; 0.2 µg/ml for 1× cultures, 0.75 µg/ml for 5× cultures, 1.5 µg/ml for 10× cultures, 3.0 µg/ml for 20× cultures, 4.5 µg/ml for 30× cultures, and 6.0 µg/ml for 40× cultures. To directly compare protein expression between different vectors at various degrees of culture condensation, each lane was loaded with the equivalent of 100 µL of uncondensed culture centrifuged and resuspended in lysis buffer (10 mM sodium phosphate pH 7.2; 1% β-mercaptoethanol; 1% SDS; 6 M urea).

Protein Purification and Mass Spectrometry.

1 ml of 40-fold condensed, $^{15}$N-enriched cultures containing either the expression plasmid pColdI(tet) cspA or pColdI(IPTG) cspA was centrifuged at 10,000×g and resuspended in 1.0 ml of lysis buffer (10 mM sodium phosphate pH 7.2; 1% β-mercaptoethanol; 1% SDS; 6 M urea). Cellular debris was pelleted by centrifugation at 12,000×g for 30 min and supernatant containing the His$_6$ tagged CspA protein was purified by binding the cellular lysate to 40 µl of Ni-NTA agarose resin. Ni-NTA resin was washed twice with 1 ml of wash buffer (50 mM Na$_2$HPO$_4$—NaH$_2$PO$_4$; 300 mM NaCl; 50 mM imidazole; 5 mM β-mercaptoethanol, pH 8.0) and eluted in 100 µl of elution buffer (50 mM Na$_2$HPO$_4$—NaH$_2$PO$_4$; 300 mM NaCl; 250 mM imidazole; 5 mM β-mercaptoethanol, pH 8.0) Purified protein samples were run on a 15% SDS-PAG followed by Coomassie Blue staining and the CspA protein band was excised. In-gel digest with trypsin was performed in 50 mM NH$_4$HCO$_3$, pH 7.9 overnight. Peptides were extracted from the gel with 60% acetonitrile, 5% formic acid, and lyophilized. Samples were then solubilized in 0.1% trifluoroacetic acid (TFA), pH 2-5-3.0 prior to LC-MS/MS mass spectrometry. Chromatography was conducted using an ultimate nano-LC system (Dionex/LC Packings) and a fritless nanoscale column (75 µm×15 cm) packed in-house with 3 nm, 200 A pore size Magic C18 stationary phase (Michrom Bioresource, Auburn, Calif.). The column was equilibrated in 0.1% formic acid (Solvent A), and samples were eluted using a linear gradient from 2% to 45% solvent B (0.1% formic acid in acetonitrile) over 30 min at a flow rate of 250 nl/min and analyzed by an LTQ linear ion trap mass spectrometer (ThermoFinnigan, San Jose, Calif.) equipped with a nanospray source (Proxeon Biosystems).

To select peptides suitable for monitoring, tryptic peptides were analyzed by MS/Zoom scan/MSMS scan; the peptide GFGFITPDDGSK (SEQ ID NO: 11) was selected for further analysis. For quantitation of isotope incorporation, the analysis was repeated with MS in profile mode. The population of peaks corresponding to the isotope labeled peptides (based on retention time and MSMS information) were integrated for peak area.

Results

Tetracycline Inducible pCold Vectors.

A series of pCold vectors were generated, separating the IPTG induction of MazF from that of the ACA-less target gene. See FIG. 1 wherein Vector features are highlighted. (A), pColdI(tet) vector map where the region shown in bold containing TEE (translation enhancing element), His Tag, and Factor Xa vary among the different pCold(tet) vectors. M13 IG, intergenic region of M13 bacteriophage; ColE1, colicinogenic factor E$_1$ for plasmid replication. (B), expanded tetO$_1$ and tetO$_2$ region depicting the tetA-tetR overlapping promoter-operator. The mutated bases within the −35 and −10 element of the tetA promoter are highlighted in red italicized font. (C), expanded multiple cloning site including suggested sequencing primers and fusion tag; S.D, Shine Delgarno sequence. (* these restriction sites are duplicated in the multiple cloning region but can be used for 3' end cloning. Xba I is also present in the tetR gene and therefore is not recommended for cloning.)

FIG. 1A graphically describes the various features of pColdI(tet). In the new pCold(tet) vectors, the lacI gene that is responsible for repressing transcription from the lac operator was replaced with the tetR gene. Expression of the tetR gene is controlled by the promoter-operator region of Tn10 that is shared with and overlaps with that of the oppositely oriented tetA gene (FIG. 1B). Modifications were therefore made to the tetR/tetA promoter-operator region in an effort to prevent RNA Polymerase binding and transcription from the tetA promoter. While leaving the −10 and −35 elements from the tetR gene intact, the −10 and −35 elements of the tetA gene, 5'-TTGACA-3' and 5'-TATTTT-3' respectively, were mutated away from consensus to 5'-GCTCTA-3' and CGCGTT-3' respectively without disrupting the neighboring tetO$_1$ and tetO$_2$ operator sequences (FIG. 1B). In order to place the cspA promoter-driven target gene under the control of the tet operator, the lac operator sequence within the cspA 5' UTR was replaced with the tet operator sequence to allow for tet repressor binding to tetO$_1$ (FIG. 1A). The resulting changes successfully allowed for the independent induction of MazF (lacI$^R$) from that of the target protein (tetR$^R$). FIG. 1C describes the multiple cloning site. Cloning of an ACA-less synthesized gene is readily obtained through the 5' Nde I site followed by insertion of an in-frame stop codon. Several enzymes within the multiple cloning site are duplicated. The 3' terminus of the target gene can utilize the BamH I site or alternative restriction enzyme sites localized in the multiple cloning site.

pCold(tet) Vector Series.

A series of pCold(tet) vectors have been generated with various features for protein expression. As described in Table 1, each vector provides a unique combination of fusion tags for protein expression and purification purposes. The translational enhancing element (TEE) encoding the amino acids MNHKV (SEQ ID NO: 12), featured in all but one of these vectors [pCold IV(tet)], has previously been shown to increase translational efficiency in cold shock mRNAs. His$_6$ tags are included for purification purposes, where pColdI(tet) encodes a Factor Xa protease cleavage site and pColdTEV(tet) encodes a TEV protease cleavage site. While proteolytic removal of the His$_6$ tag by Factor Xa from protein expressed in pColdI(tet) leaves an N-terminal His-Met as opposed to the three residues (Gly-His-Met) remaining from TEV cleavage of proteins expressed from pColdTEV(tet), the TEV protease efficiently cleaves proteins in a wide range of buffer conditions. In contrast, Factor Xa cleavage requires a specific buffer containing calcium that may decrease the solubility of the target protein. It should be noted that any desired fusion tag can be added in frame to the target gene during gene synthesis and cloned into the pColdIV(tet) vector. Together, the vectors described in Table 1 provide a range of options for protein expression and purification purposes in the cSPP system. As described in Table 1, the various fusion tags encoded in all but the pColdIV(tet) vector will alter the predicted size of the protein product between 0.76 kDa and 2.83 kDa depending on the vector.

pCold(tet) Vector Expression.

To compare protein expression from the full series of pCold(tet) vectors, an ACA-less gene construct encoding a truncated version of the C-terminal domain of the M-MuLV IN protein was cloned into the multiple cloning site of all six pCold(tet) vectors. FIG. 2 confirms that the ACA-less gene product is in fact produced in all six vectors with slight variation in the level of expression. The gel shown in FIG. 2 is representative of several independent inductions where size differences arise from the various fusion tags described in Table 1. Slight variations in culture density can be observed between cultures in FIG. 2 by observing background staining leading to the variability of intensity in the target protein band between samples.

Comparison of Expression and Culture Condensation in pCold(IPTG) and pCold(tet) Vectors.

To determine whether proteins expressed from pCold(tet) vectors not only maintained the ability to undergo culture condensation similar to the original IPTG inducible pCold (IPTG) vector, but were improved regarding homogeneity of isotope enrichment ($^{15}N$), a side by side comparison of expression and culture condensation was carried out. For comparison, the bacterial cold shock cspA gene product was expressed as an ACA-less cassette in the pColdI vector backbone under either IPTG (pColdI(IPTG)) or anhydrotetracycline (pColdI(tet)) induction. Upon reaching the correct cell density, the IPTG inducible MazF toxin was expressed for 2 hr prior to culture condensation to allow for MazF mediated degradation of cellular mRNAs and cell growth arrest. After 2 hr of MazF induction, cells were centrifuged and resuspended in various volumes of $^{15}N$-enriched M9 medium. FIGS. 3 (A and B) compares the various condensed states of protein expression resulting from the IPTG inducible (A) and tet inducible (B) pCold vectors. In both cases, little difference in expression is observed from uncondensed (1×) to 40-fold (40×) condensation. It can be concluded that expression from the pColdI(tet) vector is comparable to expression from the pColdI(IPTG) vector.

Comparing Isotope Incorporation in pCold (IPTG) and pCold (tet) Vectors.

FIGS. 4 (A and B) shows a graphical representation of the time course of induction and isotope incorporation. For the IPTG induced system, the addition of IPTG required to induce MazF expression prior to culture condensation and introduction of isotope enriched medium leads to a substantial amount of unwanted expression from the pCold(IPTG) vectors. The grey shaded region highlights the period where IPTG induced protein expression occurs in the absence of culture condensation and introduction of isotope enriched medium. The dual IPTG/tet induced system is predicted to eliminate the substantial amount of unlabeled expression from the ACA-less target gene. To confirm the improved yield of isotope enriched protein product expected with the dual induction cSPP(tet) system, mass spectrometry was performed on 40× condensed, $^{15}N$-enriched CspA protein. FIGS. 4 (C and D), displaying a representative tryptic fragment GFGFITPDDGSK (SEQ ID NO: 11) of CspA, highlights the dramatically improved ratio of isotope enriched to unenriched product when using the pColdI(tet) vector as compared to the pColdI(IPTG) vector. The predicted weight of the fully labeled, double charged peptide is 626.70 Daltons and the unlabeled peak is 621.00 Daltons. Remarkably, the 621.00 mass unit peak constitutes 20% of the total protein fraction when using the pColdI(IPTG) vector but is nearly absent, representing only 1.3% of the total protein, when using the pColdI(tet) vector. Comparison of the two plots shows that the labeling of the tetracycline induced protein (FIG. 3D) is dramatically less heterogeneous and more complete than protein expressed from the IPTG inducible pColdI vector (FIG. 3C). The fully labeled peak from the pColdI(tet) product appears at 626.81 mass units, the predicted weight for 100% isotope incorporation, compared to the 625.81 mass unit peak from product produced with the pColdI(IPTG) vector. Furthermore, the isotope enrichment is more complete as determined by comparing the width of the half height of the peak. The distribution from product produced with the pColdI(IPTG) vector ranges 2.5 mass units (representing a range of isotopic incorporation of 60-100%), whereas the peak from the pColdI(tet) vector product ranges only 1.5 mass units (representing a range of isotopic incorporation of 90-100%).

Example 2

Methods and Materials

The cSPP system utilizes MazF, a cellular endoribonuclease, to induce a quasi-dormant state within the cell. MazF specifically cleaves single-stranded RNA at ACA sequences, thereby destroying cellular mRNAs, and shutting down protein synthesis. Engineering a target gene devoid of ACA triplets therefore renders transcripts resistant to MazF cleavage. Upon expression of MazF and induction of a quasi-dormant state, it is possible to not only selectively produce a single protein in a living cell, but to do so in highly-condensed culture conditions.

General Protocol for Production of [$^1H$—$^{13}C$]-1(β1)LV, $^{13}C$, $^{15}N$, $^2H$-Enriched Proteins Using Anhydrotetracycline-Inducible SPP Vectors.

Anhydrotetracycline-inducible pCold vectors, containing target protein under the control of the tet operator ($tetO_1$), are described in reference 1. The following protocol is used for production of $^2H$-enriched proteins with these vectors.

(i) Pick a single colony (containing pMazF and the expression plasmid), using a toothpick, from freshly plated transformed cells grown overnight on MJ9-CAA medium based plates (MJ9 medium supplemented with 0.2% casamino acids) containing 25 μg/mL chloramphenicol and 100 μg/mL ampicillin at 37° C. and inoculate MJ9-CAA medium for overnight growth on a shaker (at approximately 180 r.p.m.). Throughout this protocol, the MJ9 medium, which is vitamin and buffer supplemented[2], can be replaced with standard M9 medium, though better protein expression yields are usually obtained with MJ9 medium.

(ii) Inoculate MJ9 medium containing 25 μg/mL chloramphenicol and 100 μg/mL ampicillin at 5 μL/mL (CAA should NOT be added). Grow cultures overnight at 37° C. on a shaker (at approximately 180 r.p.m.).

(iii) Inoculate 10% of desired culture volume from overnight culture into fresh MJ9 medium containing 25 μg/mL chloramphenicol and 100 μg/mL ampicillin, and incubate at 37° C. on a shaker (at approximately 180 r.p.m.). Note: if protein is to be labeled with specific amino acids or precursors, the same unlabeled amino acids or precursors (see b. below) should be added at this time to suppress the corresponding biosynthesis pathways from glucose during cell culture growth.

Specifically, for preparations labeling the isopropyl methyl groups of Leu and Val, add 100 mg/L a-ketoisovaleric acid; for preparations labeling Ile, add 50 mg/L a-ketobutyric acid (Ile); for preparations labeling Phe, Tyr, or Trp, add 75 mg/L shikimic acid or 50 mg/L of the individual amino acids Phe, Tyr, and/or Trp, to suppress the corresponding biosynthetic pathways.

(iv) Monitor the optical density of the culture at 600 nm. The initial $OD_{600}$ should be approximately 0.2 after inoculation. Make sure the culture is growing exponentially. The $OD_{600}$ of the culture should increase linearly in a graph of log $OD_{600}$ verses time.

(v) When the $OD_{600}$ reaches ~0.5, remove the flask from the shaker and chill the culture rapidly by shaking the flask in an ice water bath for 10 min to reach a target temperature of 15° C.

(vi) Add IPTG to a final concentration of 1 mM to induce expression of MazF. Harvest a sample of cells from 1.5 mL of the culture by centrifugation (12,000×g, 5 min, 4° C.) and store the resulting pellet at −20° C. for subsequent analysis of protein expression levels by SDS-PAGE.

(vii) Continue the culture at 15° C. with shaking for 2 more hours. This 2 hour pre-incubation step before culture condensation and isotope labeling is important to prevent background isotope incorporation and prepare the cells for subsequent condensation.

(viii) Centrifuge (5000×g, 10 min, 4° C.) the culture to collect the cells and resuspend the cell pellet at 2.5% the initial culture volume (40×) in chilled 100 mM phosphate buffer, pH 7.5, in $^2H_2O$ to wash the cells. Repeat centrifugation step to re-pellet the cells.

(ix) Resuspend the cell pellet in the desired culture volume of MJ9 medium prepared in $^2H_2O$, and containing specifically labeled amino acids or precursors together with 25 μg/mL chloramphenicol, 100 μg/mL ampicillin, 1 mM IPTG and anhydrotetracycline (see b. below for anhydrotetracycline concentration). For production of [$^1H$—$^{13}C$]—I(δ1)LV,$^{13}C$, $^{15}N$, $^2H$-enriched proteins, the condensed fermentation contains 1 g/L $^{15}N$—NH$_4$Cl; 4 g/L $^{13}C,^2H$-glucose; 50 mg/L a-$^{13}C$-ketobutyric acid; 100 mg/L a-$^{13}C$-ketoisovaleric acid. For labeling of Phe, Tyr, and/or Trp [$^1H$, $^{13}C$]-enriched sites, add 75 mg/L of $^1H$, $^{13}C$-enriched shikimic acid or 50 mg/L each of isotopically-enriched Phe, Tyr, and/or Trp amino acids.

a. The degree of condensation allowing for optimal expression varies among the different proteins expressed (FIG. 5). 20-fold condensed (5% of initial volume) is a good starting point; however, optimal fold condensation can be worked out in small scale pilot experiments if it is desired. Dilute a portion of the condensed culture to have approximately 5 mL at 1× and induce separately for an uncondensed control.

b. Uncondensed cultures should be induced with 0.2 μg/mL of anhydrotetracycline. Culture condensation requires that the concentration of anhydrotetracycline is increased linearly up to 20× condensation. To calculate this, take the fold condensation of the culture and multiply by 0.15 μg/mL of anhydrotetracycline. For example, a 20× condensed culture would require (20*0.15 μg/mL=3.0 μg/mL) of anhydrotetracycline for induction.

(x) Incubate the condensed culture at 15° C. with shaking overnight. Harvest the cell pellet by centrifuging (12,000× g, 5 min, 4° C.) and store them at −80° C.

General Protocol for Production of [$^1H$—$^{13}C$]—I(δ1)LV, $^{13}C$, $^{15}N$, $^2H$-Enriched Proteins Using IPTG-Inducible SPP Vectors.

Using IPTG inducible pCold vectors, available from Takara Bioscience, the protocol for production of $^2H$-enriched proteins is essentially identical to that used for the anhydrotetracycline-induced vectors, except that no anhydrotetracycline is added in step (ix).

Preparation of [1H—$^{13}C$]—I(δ1)LV, $^{13}C$, $^{15}N$, $^2H$-CspA for Structural Studies.

Isotope-enriched samples of CspA were prepared as described in the protocol above, with the following details. Competent *E. coli* BL21(DE3) cells containing the pACY-CmazF plasmid were transformed with pColdI(SP-4) plasmid (Takara Bioscience, Inc) containing ACA-less cspA cloned into the Nde I-BamHI sites. The resulting constructs include a 16-residue N-terminal tag, consisting of a translation enhancing element (TEE), a His$_6$ tag, and a Factor Xa cleavage site. Protein expression was performed essentially as described above, with the following details: single colonies were selected and used to inoculate 2.5 mL LB medium at 37° C. for 6 hrs. 2 mL of the LB culture was inoculated into 100 mL of MJ9 minimal medium at 37° C. overnight. When $OD_{600}$ reached 1.8-2.0 units, the culture was centrifuged at 3000×g for 15 min at 4° C. The cell pellet was resuspended in 1 L of fresh MJ9 medium and cells were grown at 37° C. until $OD_{600}$ reached 0.5. At this point the culture was chilled on ice for 5 min and shifted to 15° C. for 45 min to acclimate the cells to cold shock conditions. Target protein (CspA) was then expressed along with MazF for 1.5 hrs by addition of 1 mM isopropyl-β-D-thiogalactoside (IPTG) prior to expression in isotope enriched medium. Cultures were then centrifuged at 3000×g for 15 min at 4° C., resuspended in 2.5% volume (40×) in deuterated ($^2H_2O$) wash solution (7.0 g/L Na$_2$HPO$_4$; 3.0 g/L KH$_2$PO$_4$; 0.5 g/L NaCl; pH 7.4)], centrifuged again, and resuspended in 25 mL of deuterated MJ9 minimal medium containing 1 g/L $^{15}$NH$_4$Cl; 4 g/L $^{13}C,^2H$-glucose; 50 mg/L a-$^{13}C$-ketobutyric acid; 100 mg/L a-$^{13}C$-ketoisovaleric acid; and 1 mM IPTG. Protein expression continued at 15° C. for 24 hrs. Cells were harvested by centrifugation as described above and cell pellets were stored at −80° C. For SDS-PAGE analysis, 100 μL of uncondensed cell culture (1×) or 2.5 μL of 40-fold condensed cultures (40×) were analyzed by Coomassie Blue stain. All isotopes were purchased from Cambridge Isotope Laboratories.

CspA Purification and Concentration.

Cell pellets were resuspended in 40 mL of lysis buffer [50 mM Na$_2$HPO$_4$—NaH$_2$PO$_4$; 300 mM NaCl; 5 mM imidazole; 5 mM 2-mercaptoethanol (βME); with 1 EDTA-free protease inhibitor tablet (Roche Cat. #11 873 580 001) per 50 mL at pH 8.0] and sonicated to lyse the cells. Lysed cells were then centrifuged at 4° C. for 1 hr at 16,000 rpm in a Sorvall SS-34 rotor. Proteins were further purified by binding to NiNTA agarose at 40 mL of soluble extract per 1 mL of bed resin at 4° C. overnight. Resin was washed twice with 25 mL of wash buffer [50 mM Na$_2$HPO$_4$—NaH$_2$PO$_4$; 300 mM NaCl; 25 mM imidazole; 5 mM 2-mercaptoethanol (βME), pH 8.0], and protein was eluted in 8 mL of elution buffer [50 mM Na$_2$HPO$_4$—NaH$_2$PO$_4$; 300 mM NaCl; 300 mM imidazole; 5 mM 2-mercaptoethanol (βME), pH 8.0]. The protein solution was then dialyzed overnight at 4° C. into NMR buffer (20 mM Na$_2$HPO$_4$—NaH$_2$PO$_4$, 50 mM KCl, 0.02% NaN$_3$, 5 mM MgCl$_2$, pH 7.0 for EnvZB, and 50 mM KH$_2$PO$_4$, 1 mM NaN$_3$, adjusted to pH 6.0 with 5 M KOH for CspA). Protein solutions were then concentrated with Amicon Ultra 4 centrifugal filter devices (5000 MWCO) by centrifugation (2500×g) to a volume of 1 mL. 3 mL of NMR buffer containing and 5% $^2H_2O$ was added and samples were again centrifuged to 1 mL. This process was repeated and samples were further concentrated to a volume of 500 μL at a final concentration of 2-3 mg/mL (~0.2 mM) for NMR studies.

Expression of *E. coli* Plasma Membrane Protein YaiZ in cSPP System.

Uniformly $^2H$, $^{13}C$, $^{15}N$-enriched YaiZ was prepared according to the protocol describe above, with the following details. *E. coli* BL21 (DE3) cells, transformed with pACY-CmazF and pColdI(SP-4) plasmids harboring the ACA-less yaiZ target gene, were grown in M9-glucose medium at 37° C. When $OD_{600}$ reached 0.5-0.6 units, the culture was chilled on ice for 5 min and shifted to 15° C. for 45 min in order to acclimate the cells to cold temperature. After the cold-shock treatment, the expression of both MazF and the target gene were induced with 1 mM isopropyl β-D-1-thiogalactopyranoside (IPTG). The cell pellet was washed twice with 10 mL of M9 salt buffer (no $NH_4Cl$) in $^2H_2O$, and finally suspended in 50 mL of deuterated M9 minimal medium (20× condensed phase) containing 1 g/L $^{15}NH_4Cl$; 4 g/L $^{13}C$, $^2H$-glucose, and 1 mM IPTG. Protein production was induced at 15° C. for ~36 hr and the cells were then harvested by centrifugation.

Expression of *E. coli* Outer Membrane Protein OmpX in cSPP System.

Uniformly $^2H$, $^{13}C$, $^{15}N$-enriched OmpX was prepared according to the protocol describe above, with the following details. An ACA-less gene coding for *E. coli* outer membrane protein OmpX was cloned into pColdIV(SP-4). *E. coli* strain BL21(DE3) was engineered to be ompA and ompF for two major outer membrane proteins, a strategy aimed at enhancing target outer membrane protein expression. These *E. coli* BL21(DE3) cells were transformed with pACYC-mazF and pColdI(SP-4) plasmids harboring the target gene and grown in 2 L M9-glucose medium at 30° C. When $OD_{600}$ reached 0.5-0.6 units, the culture was chilled on ice for 5 min and shifted to 15° C. for 45 min in order to acclimate the cells to cold temperature. After the cold-shock treatment, the expression of both MazF and the target gene were induced with 1 mM isopropyl β-D-1-thiogalactopyranoside (IPTG) for 45 min. The cells were then harvested by centrifugation at 3000×rpm for 30 min at 4° C. The cell pellet was washed twice with 10 mL of M9 salt buffer (no $NH_4Cl$) in $^2H_2O$, and finally suspended in 50 mL of deuterated M9 minimal medium (40× condensed phase) containing 1 g/L $^{15}NH_4Cl$; 4 g/L $^{13}C$, $^2H$-glucose, and 1 mM IPTG. Protein production was induced at 15° C. for 36 hr and the cells were then harvested by centrifugation.

NMR Sample Preparation of YaiZ.

The cell pellet provided by a 20× condensed culture originating as a 1 L fermentation was suspended in 10 nil of 50 mM Tris buffer (pH 7.4). Cells were then lysed by a French press at 15,000 psi. The membrane fraction was collected by centrifugation at 100,000×g for 1 hr at 4° C. The membrane pellet was resuspended in 1 ml of 50 mM Tris buffer (pH 7.4) by sonication, centrifuged at 100,000×g for 1 hr at 4° C. and the membrane pellets were stored at −80° C. The NMR sample of [$^2H$, $^{13}C$, $^{15}N$]-YaiZ was prepared by simple detergent solubilization of the plasma membrane fraction by 25 mM MES buffer, pH 6.0, containing 10% LOPG in 95% $H_2O$/5% $^2H_2O$. The final concentration of YaiZ in the NMR sample was ~0.2 mM.

NMR Sample Preparation of OmpX.

The cell pellet provided by a 40× condensed culture originating as a 1 L fermentation was suspended in 4 mL of 20 mM potassium phosphate buffer, pH 6.4, containing 0.5% sodium lauryl sarcosinate (Sarkosyl) and incubated at room temperature for 20 min, followed by centrifugation at 135,000×g for 30 mM at 4° C. The outer membrane fraction, was then isolated as a pellet[10]. The NMR sample of [$^2H$, $^{13}C$, $^{15}N$]-OmpX was then prepared by simple detergent extraction from the outer membrane fraction using 20 mM potassium phosphate buffer, pH 6.4, containing 5% DPC and 5% $^2H_2O$. The sample was briefly treated at about 80° C. to allow extensive back-exchange of amide protons. The final concentration of OmpX in the NMR sample was ~0.2 mM.

Mass Spectrometry for Analysis of Isotope Incorporation.

Purified protein samples were run on a 15% SDS-PAGE followed by Coomassie Blue staining. In-gel digest was performed in 50 mM $NH_4HCO_3$, pH-7.9 overnight. Peptides were extracted from the gel with 60% acetonitrile, 5% formic acid, and lyophilized. Samples were then solubilized in 0.1% trifluoroacetic acid (TFA), pH 2.5-3.0, prior to liquid chromatography mass spectrometry/mass spectrometry (LC-MS/MS) analysis. Chromatography was done using an ultimate nano-LC system (Dionex/LC Packings) and a fritless nanoscale column (75 μm×15 cm) packed in-house with 3 μm, 200 A pore size Magic C18 stationary phase (Michrom Bioresource, Auburn, Calif.). The column was equilibrated in 0.1% formic acid (Solvent A), and samples were eluted using a linear gradient from 2% to 45% solvent B (0.1% formic acid in acetonitrile) over 30 min at a flow rate of 250 nL/min and analyzed by an LTQ linear ion trap mass spectrometer (ThermoFinnigan, San Jose, Calif.) equipped with a nanospray source (Proxeon Biosystems).

To select peptides suitable for monitoring isotopic enrichment, the tryptic peptides were analyzed by MS/Zoom scan/MSMS scan. For EnvZB, peptide TISGTGL-GLAIVQR (SEQ ID NO: 2) was selected, for CspA, peptide SLDEGQKVSFTIESGAK (SEQ ID NO: 1) was selected, and for MuLV IN NTD, peptide $SHSPYYM_{(oxidation)}LNR$ (SEQ ID NO: 3) was selected. Quantitation of isotope incorporation was performed with MS in profile mode, by integration of peak areas. The percent of isotope incorporation was determined by comparing the mass estimated from the isotope-enriched peptide mass distribution to the expected mass computed assuming 100% isotope (and/or methyl $^1H$) incorporation. These EnvZB and CspA proteins were expressed in $^{13}C$, $^{15}N$, $^2H$ enriched medium with $^{13}C$—$^1H$ labeled precursors to the methyl groups of Ile(δ1), Leu, and Val. It is therefore expected that all of the carbon and nitrogen atoms present in a fully-enriched samples are $^{13}C$ and $^{15}N$ isotopic forms, the targeted methyls are $^1H$ forms, and all of the rapidly-exchanging atoms will back-exchange to $^1H$ when purified in $H_2O$ buffers. Therefore, all NH, SH, and OH groups, along with the methyl protons of Ile(δ1), Leu, and Val residues, are assumed to be $^1H$ isotopes in the fully isotope-enriched peptide fragments. To specifically determine the percent of deuterium incorporation and precursor incorporation independently, the MuLV IN NTD was expressed in $2H_2O$ medium without protonated precursors for the amino acids isoleucine, leucine, and valine. The peptide $SHSPYYM_{(oxidation)}LNR$ (SEQ ID NO: 3) was then analyzed to determine the efficiency of $^2H$ incorporation.

NMR Spectroscopy.

NMR measurements of uniformly 2H, $^{15}N$ enriched YaiZ in 10% LOPG were obtained using an 800 MHz Bruker AVANCE spectrometer with a cryoprobe at 40° C. TROSY [$H^N$—$^{15}N$] HSQC NMR data were acquired using spectral widths of 14 ppm in $^1H$ dimension and 32 ppm in $^{15}N$ dimension. The matrix size of collected spectra was 1024× 256 total data points. NMR measurements of uniformly $^2H$, $^{13}C$, $^{15}N$-enriched OmpX in 5% DPC were obtained using a 600 MHz Bruker AVANCE spectrometer with a cryoprobe at 50° C. TROSY [$H^N$—$^{15}N$] HSQC NMR data were acquired using spectral widths of 14 ppm in $^1H$ dimension and 34 ppm in $^{15}N$ dimension. The matrix size of collected spectra was 1024×256 total data points. NMR spectra of CspA and EnvZB were recorded at 20° C. using an 800 MHz Bruker AVANCE spectrometer with cryogenic probe, except where noted otherwise. Non-constant time [$^{13}C$—$^1H$]-HSQC spectra were acquired for both CspA and EnvZB with [$^1$H—$^{13}$C]—I($\delta$1)LV, $^{13}$C, $^{15}$N, $^2$H-enrichment. Resonance assignments for [$^1$H—$^{13}$C]—I($\delta$1)LV, $^{13}$C, $^{15}$N, $^2$H-enriched CspA were determined using conventional triple resonance NMR experiments, including HNCO and deuterium-decoupled pulse sequences HN(ca)CO; HNCA; HN(co)CA; HNCACB and HN(co)CACB. The carrier positions were set to 118.0 ppm for $^{15}$N, 176 ppm for $^{13}$CO, 54 ppm for $^{13\alpha}$ and 39 ppm for $^{13\alpha}/^{13}C^\beta$. Key parameters of data collection are summarized in Table 2.

sign for automated analysis of backbone resonance assignments. Side chain $^{13}$C and $^1$H methyl resonances of Leu, Val and Ile ($\delta$1) were determined subsequently by interactive spectral analysis using [$^{13}$C—$^1$H]-HSQC, 3D $^{13}$C-edited NOESY, and 3D $^{15}$N-edited NOESY spectra.

Generating Protein Structures Using Chemical-Shift Based Protein Structure Prediction by ROSETTA (CS-ROSETTA).

Chemical shift information, including backbone $^{13}C^\alpha$, $^{15}$N, $^{13}$C', $^1H^N$ and side chain $^{13}C^\beta$ assignments, were used as input for CS-ROSETTA. Three key steps are involved.

TABLE 2

800 MHz Triple resonance data used for determining backbone resonance assignments.

| | $^{15}$N-HSQC | HNcoCA | HNCO | HNCA | HNCACB | HNcoCACB | HNcaCO |
|---|---|---|---|---|---|---|---|
| No. of points | | | | | | | |
| Collected | 1024, 256 | 1024, 40, 50 | 1024, 40, 40 | 1024, 40, 50 | 1024, 64, 100 | 1024, 40, 100 | 1024, 40, 40 |
| After LP | 1024, 512 | 1024, 72, 82 | 1024, 72, 72 | 1024, 72, 82 | 1024, 96, 164 | 1024, 96, 164 | 1024, 72, 72 |
| After zero filling | 1024, 512 | 1024, 128, 128 | 1024, 128, 128 | 1024, 128, 128 | 1024, 128, 256 | 1024, 128, 256 | 1024, 128, 128 |
| No. of scans | 8 | 4 | 4 | 4 | 16 | 16 | 16 |
| Spectral width ($\omega_1$, $\omega_2$, $\omega_3$; ppm) | 14, 28 | 14, 23, 32 | 14, 23, 24 | 14, 23, 32 | 14, 28, 72 | 14, 28, 72 | 14, 23, 24 |
| Recycle delay (s) | 1 | 1 | 1 | 1 | 1 | 1 | 1 |
| Collection time (h) | 0.6 | 2.2 | 2.0 | 2.2 | 33.2 | 33.6 | 8.6 |

The total data collection time for all of these triple resonance experiments was about 3.5 days. In addition, 3D $^{13}$C-edited NOESY (mixing time of 350 ms) and $^{15}$N-edited NOESY (mixing time of 175 ms) were collected on a 600 MHz Bruker spectrometer with TXT probe. The matrix sizes of these spectra were 1024×32×220 total data points for $^{13}$C-edited NOESY, and 1024×64×256 total data points for $^{15}$N-edited NOESY. For $^{13}$C-edited NOESY, the spectrum widths in $^1$H, $^{13}$C and indirect detected $^1$H dimensions were set to 14 ppm, 16 ppm and 12 ppm respectively and the carrier positions were set 4.7 ppm for $^1$H and 16 ppm for $^{13}$C dimension. For $^{15}$N-edited NOESY, the spectrum widths in $^1$H, $^{15}$N and indirect detected $^1$H dimensions were set to 14 ppm, 28 ppm and 11.5 ppm respectively and the carrier positions were set 4.7 ppm for $^1$H and 118 ppm for $^{15}$N dimension. In all NMR experiments, FIDs were processed with linear prediction and zero filling, and weighted by sine bell function in all direct and indirect detected dimensions. All NMR spectra were processed and examined with NMRPipe and NMRDraw software package. The program SPARKY was used for data visualization and analysis. Chemical shifts of proton were referenced to external DSS. $^{13}$C and $^{15}$N chemical shifts were referenced indirectly based on the proton referencing.

Analysis of Resonance Assignments.

AutoAssign software was used for semi-automated analysis of backbone and side chain $^{13}C^\beta$ resonance assignments for CspA. Peak list of [$^{15}$N—$^1H^N$]-HSQC, and peak lists from the triple resonance experiments, including 3D HNCO; HN(ca)CO; HNCA; HN(co)CA; HNCACB and HN(co)CACB, were peak picked automatically using the 'restrictive peak picking' function of the SPARKY software; these peak lists were manually refined prior to input into AutoAs- First, based on the chemical shift values and protein sequences, peptide fragments were selected from a protein structure database using the MFR module of the NMRPipe software package. All proteins with PSI-BLAST e-score <0.05 with E. coli CspA were removed from the database. Second, a standard ROSETTA protocol was used for de novo structure generation. Third, ROSETTA all-atom models resulting from the above procedure were evaluated based on how well the predicted chemical shifts using SPARTA agree with the experimental chemical shifts. If the lowest energy models cluster within less than ~2 Å from the model with the lowest energy, the structure prediction is considered successful and lowest energy models are converged. A total of 10,000 all-atom Rosetta models were generated from the MFR-selected peptide fragments, using a cluster of 20 CPUs. The 1,000 lowest-energy models were chosen and their all-atom ROSETTA energies were recalculated in terms of the fitness with respect to the experimental chemical shift values. The lowest energy models are converged based on the fact that ° rmsd values are less than ~2 Å relative the lowest energy model. 10 lowest energy models were selected as a representation of the 3D structure of CspA. The CS-ROSETTA package used in this work may be downloaded from http://spin.niddk.nih.gov/baxlsoftware/C SRO SETTA/indes.html.

Conventional 3D Structure Calculations.

Conventional 3D structure calculations were performed using the AutoStructure software ver. 2.2.1-CND for automated analysis of NOESY cross peak assignments, implemented together with the program CYANA ver. 2.1 for structure generation. The input for AutoStructure analysis consisted of (1) a list of backbone and $^{13}$C—$^1$H methyl side chain assignments; (2) manually edited NOESY peak lists, including chemical shift and peak heights, generated from $^{13}$C-edited and $^{15}$N-edited NOESY spectra; (3) locations of slowly exchanging amide hydrogens based on published amide $^{1}$H/$^{2}$H exchange data for CspA; (4) broad ϕ, ψ angle constraints (±40° and ±50°, respectively) derived from chemical shift data (after correction of $^{2}$H isotope-shift effect) using the program TALOS. The best 10 of 56 structures (lowest energy) from the final cycle of AutoStructure were refined by restrained molecular dynamics in an explicit water bath using CNS 1.1.

TABLE 3

Summary of Structural Statistics for *E. coli* CspA Structures[a]

| | Sparse-constraint NMR Structure[b] | Conventionally-determined NMR Structure[c] | Sparse-constraint CS-Rosetta Structure[d] |
|---|---|---|---|
| Conformationally-restricting constraints[e] | | | |
| Distance constraints | | | |
| Total | 131 | | 131 |
| intra-residue (i = j) | 17 | | 17 |
| sequential (\|i − j\| = 1) | 45 | | 45 |
| medium range (1 < \|i − j\| ≤ 5) | 8 | | 8 |
| long range (\|i − j\| > 5) | 61 | | 61 |
| distance constraints per residue | 2.0 | | 2.0 |
| Dihedral angle constrains | 68 | | 68 |
| Hydrogen bond constraints | | | |
| Total | 22 | | 22 |
| long range (\|i − j\| > 5) | 20 | | 20 |
| Number of constraints per residue | 3.3 | | 3.3 |
| Number of long range constraints per residue | 1.2 | | 1.2 |
| Residual constraint violations[e] | | | |
| Average number of distance violations per structure | | | |
| 0.1-0.2 Å | 1.4 | | 0.9 |
| 0.2-0.5 Å | 0 | | 1.9 |
| >0.5 Å | 0 | | 3.7 |
| average RMS distance violation/constraint (Å) | 0.02 | | 0.17 |
| maximum distance violation (Å) | 0.18 | | 1.74 |
| Average number of dihedral angle violations per residue | | | |
| 1-10° | 3.6 | | 3 |
| >10° | 0 | | 0.8 |
| average RMS dihedral angle violation/constraint (°) | 0.45 | | 1.73 |
| maximum dihedral angle violation (°) | 3.4 | | 16.70 |
| RMSD from average coordinates (Å)[e,f] | | | |
| backbone atoms | 1.2 | 0.5 | 0.8 |
| heavy atoms | 1.7 | 1.1 | 1.2 |
| RMSD from X-ray structure (Å)[e,g] | | | |
| backbone atoms | 1.58 ± 0.38 | 0.95 ± 0.11 | 0.52 ± 0.12 |
| heavy atoms | 2.24 ± 0.34 | 1.83 ± 0.16 | 1.17 ± 0.11 |
| Sidechain RMSD from X-ray structure (Å)[e,h] | | | |
| heavy atoms | 1.76 ± 0.20 | 1.59 ± 0.15 | 0.86 ± 0.11 |
| heavy sidechain atoms | 1.81 ± 0.23 | 1.93 ± 0.22 | 1.14 ± 0.12 |
| Ramachandran statistics[e,f] | | | |
| most favored regions (%) | 92.0 | 78.3 | 93.7 |
| additional allowed regions (%) | 8.0 | 21.7 | 6.3 |
| generously allowed (%) | 0.0 | 0.0 | 0.0 |
| disallowed regions (%) | 0.0 | 0.0 | 0.0 |
| Global quality Scores[e] | Raw/Z-score | Raw/Z-score | Raw/Z-score |
| Verify 3D | 0.33/−2.09 | 0.43/−0.48 | 0.45/−0.16 |
| Prosall | 0.61/−0.17 | 0.77/0.50 | 0.85/0.83 |
| Procheck (phi-psi)[e] | −0.49/−1.61 | −1.37/−8.07 | −0.26/−0.79 |

TABLE 3-continued

Summary of Structural Statistics for E. coli CspA Structures[a]

| | Sparse-constraint NMR Structure[b] | Conventionally-determined NMR Structure[c] | Sparse-constraint CS-Rosetta Structure[d] |
|---|---|---|---|
| Procheck (all dihedrals)[e] | −0.42/−2.48 | −1.47/−8.69 | 0.00/0.00 |
| Molprobity clash score | 15.22/−1.09 | 64.74/−9.58 | 5.58/0.57 |

[a]Analysis for residues 1 to 70, excluding disordered N-terminal expression tag.
[b]Structure obtained from sparse NMR constraints. NMR structure determined by conventional methods (PDB id 3mef)
[d]Structure obtained from CS-Rosetta structure generation, compared with constraints; note that these distance constraints were not used in generating the CS-Rosetta structure
[e]Generated using PSVS 1.3 program. Average distance violations were calculated using the sum over r[−6]. Note that the conformational constraints were not used in CS-Rosetta calculations except to validate the structure by providing the statistics listed in this table.
[f]Order residue ranges [S(phi) + S(psi) > 1.8]. NMR structure using minimum constraints: 4-24, 30-33, 35-36, 45-46, 51-55, 63-64, 67-69; Conventionally-determined NMR structure: 4-10, 20-23, 30-32, 48-51, 53-54, 68-69; CS-Rosetta generated structure: 4-27, 29-37, 40-60, 62-66.
[g]Well-defined core region: 5-9, 19-22, 50-56, 63-69.
[h]Buried hydrophobic residues: V9, I21, V30, V32, I37, L45, V51, F53, A64, V67.

Results

Figure 14:
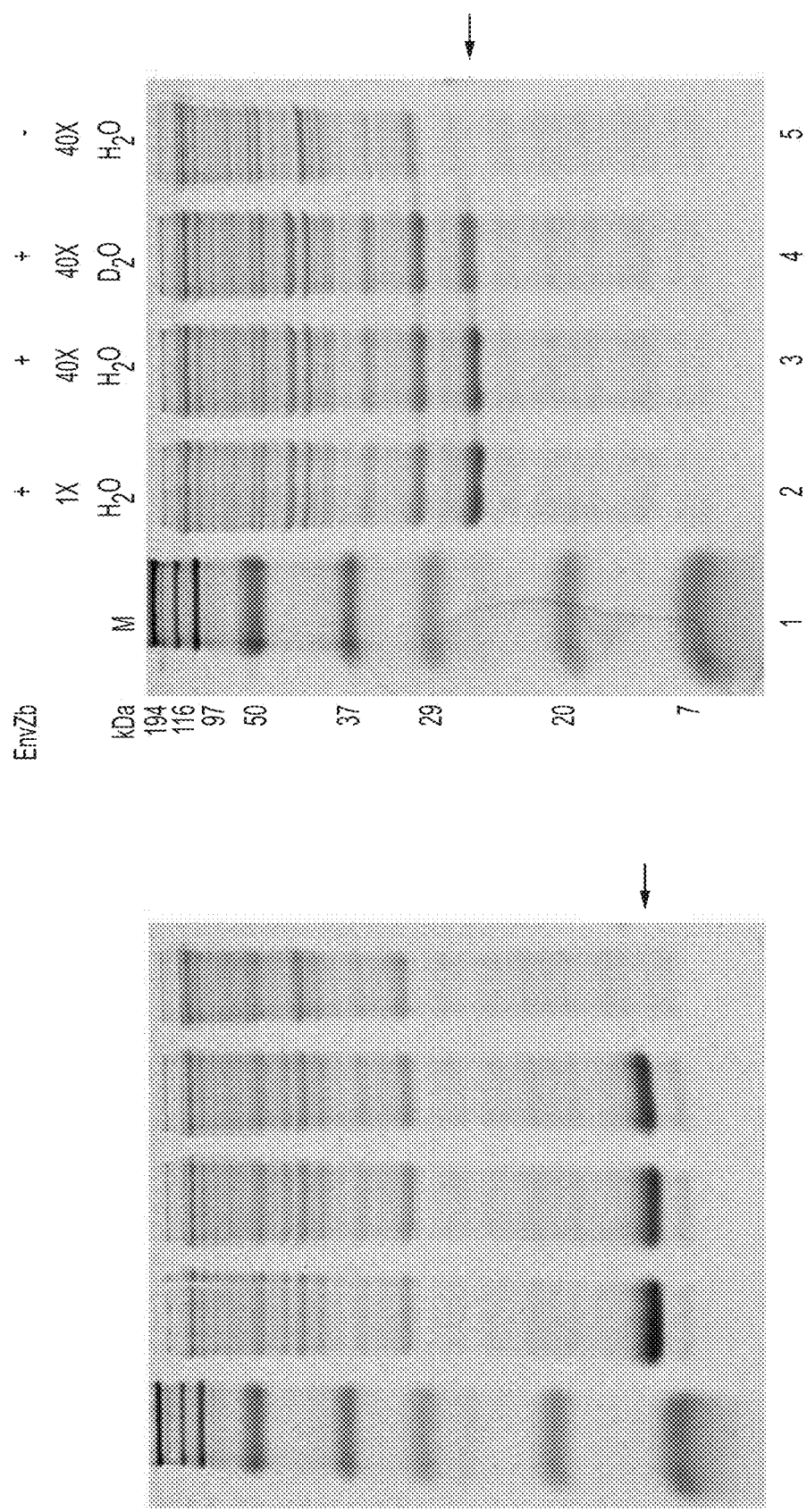
FIG. 14 depicts a coomassie stained SDS-PAGE analysis of protein expression for CspA (a) and EnvZB (b) in *E. coli* in minimal medium. Lanes 2-5 contain the whole cell extract equivalent to 100 µL of uncondensed culture. Lane 1, molecular weight marker (M); lane 2, uncondensed expression in H$_2$O; lane 3, 40-fold condensed in H$_2$O; lane 4, 40-fold condensed in $^2$H$_2$O; lane 5, 40-fold condensed control cells (without pCold I expression vector). Arrows mark CspA and EnvZB protein band accordingly. These data demonstrate cost effective production of $^2$H-enriched proteins in condensed cultures, without acclimation of *E. coli* cells, using only 2.5% of media costs compared to a conventional fermentation to obtain similar protein yields.

In order to compare protein expression levels in deuterium-based minimal medium under condensed culture conditions, two *E. coli* proteins, CspA (MW 9.4 kDa) and EnvZB (MW 19.5 kDa) were chosen for in depth analysis. Data for nine (9) additional proteins expressed in condensed culture conditions (including membrane proteins, viral proteins, and eukaryotic proteins) are shown in (FIG. 5). FIG. 14 demonstrates the effect of condensation and IPTG-induction of these two ACA-less target genes under conditions of growth arrest and cessation of cellular protein production. The levels of CspA and EnvZB produced per cell from a 40-fold (40×) condensed $H_2O$-based culture is comparable to that of the uncondensed (1×) culture, where cells were treated identically differing only in the volume of media used for resuspension during the protein expression induction phase (FIGS. 1 *a* and *b*, lanes 2 and 3). CspA protein production is also unaffected by expression in 40× condensed $^2H_2O$-based medium, while EnvZB displays only a modest reduction in expression (FIGS. 1 *a* and *b*, lane 4). A second independent analysis of EnvZB at 20× and 40× condensation showed no observable decrease in expression in $^2H_2O$-based medium (FIG. 5, panel f). These data demonstrate that no acclimation of *E. coli* cells is required for preparing perdeuterated proteins at high yield in condensed phase using the cSPP system.

Figure 6A:
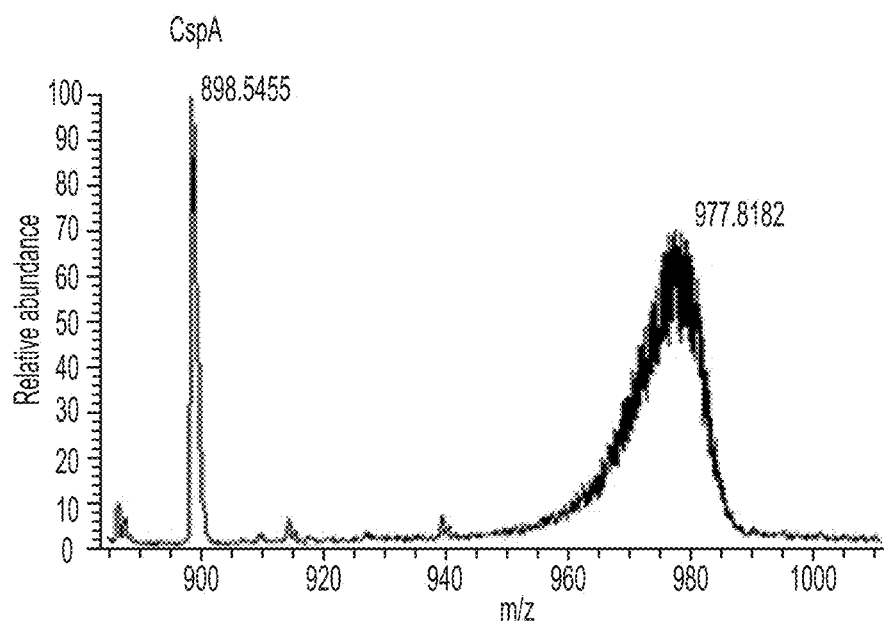
FIGS. 6A and 6B depict deuterium incorporation with protonated ILV(8) methyl groups using IPTG-induced system. LTQ linear ion trap mass spectrometry data documenting extensive $^2$H incorporation using the IPTG-induced cSPP system. (a) CspA trypsin fragment SLDEGQKVS-FTIESGAK (SEQ ID NO: 1) (Z=+2). The unlabeled peak (~10% of the sample) appears at 898.5 mass units. (b) EnvZB trypsin fragment TISGTGLGLAIVQR (SEQ ID NO: 2) (Z=+2). Unlabeled peak (~20% of the sample) appears at 693.4 mass units. Similar results were obtained using other peptide fragments. Despite the production of some unlabeled material, the IPTG-induced system provides ~85% of target protein with an average enrichment of ~85% with $^2$H, $^{15}$N, $^{13}$C, and $^1$H-methyls.
Figure 6B:
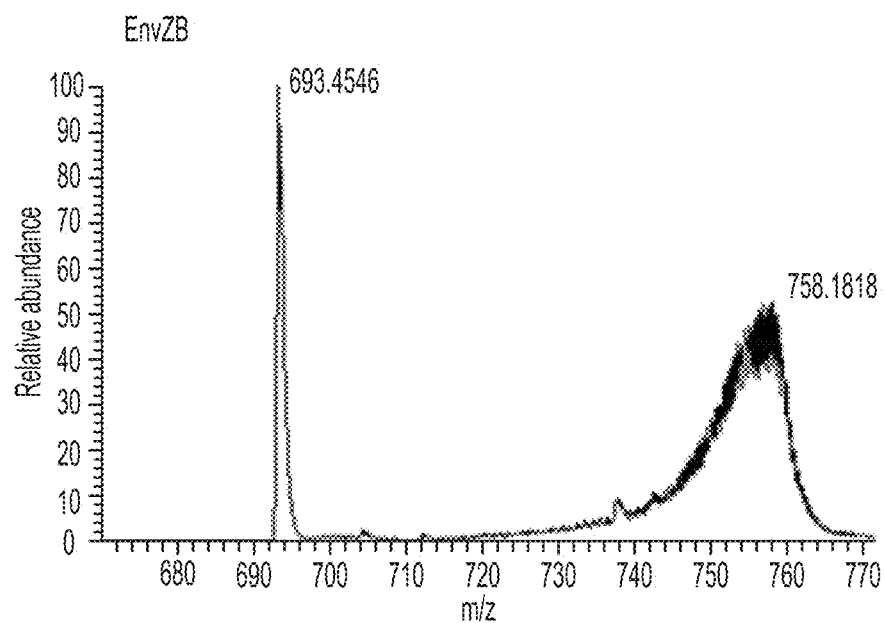
Figure 7:
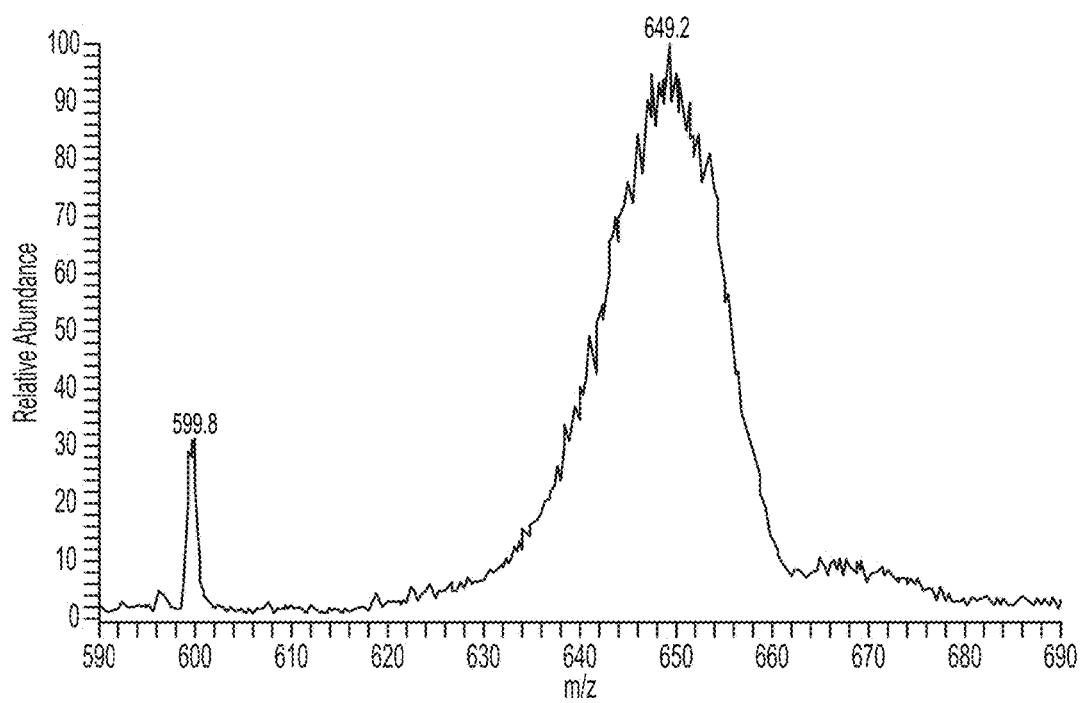
FIG. 7 depicts deuterium incorporation with protonated ILV(δ) methyl groups using dual IPTG/Tet-induced system. LTQ linear ion trap mass spectrometry data documenting extensive $^2$H incorporation using the dual IPTG/Tet-induced cSPP system, with MazF under control of IPTG and CspA under control of anhydrotetracycline. The dual control system exhibits less production of unlabeled target protein, demonstrated here with data for CspA trypsin fragment SLDEGQKVSFTIESGAK (SEQ ID NO: 1) (z=+3). The unlabeled peak at 599.8 mass units represents <3% of the sample. The mass distribution of labeled species indicate a range of enriched species of 70-100%, with an average enrichment of ~85% with $^2$H, $^{15}$N, $^{13}$C, an $^1$H-methyls. Similar results were obtained using other peptide fragments.
Figure 8:
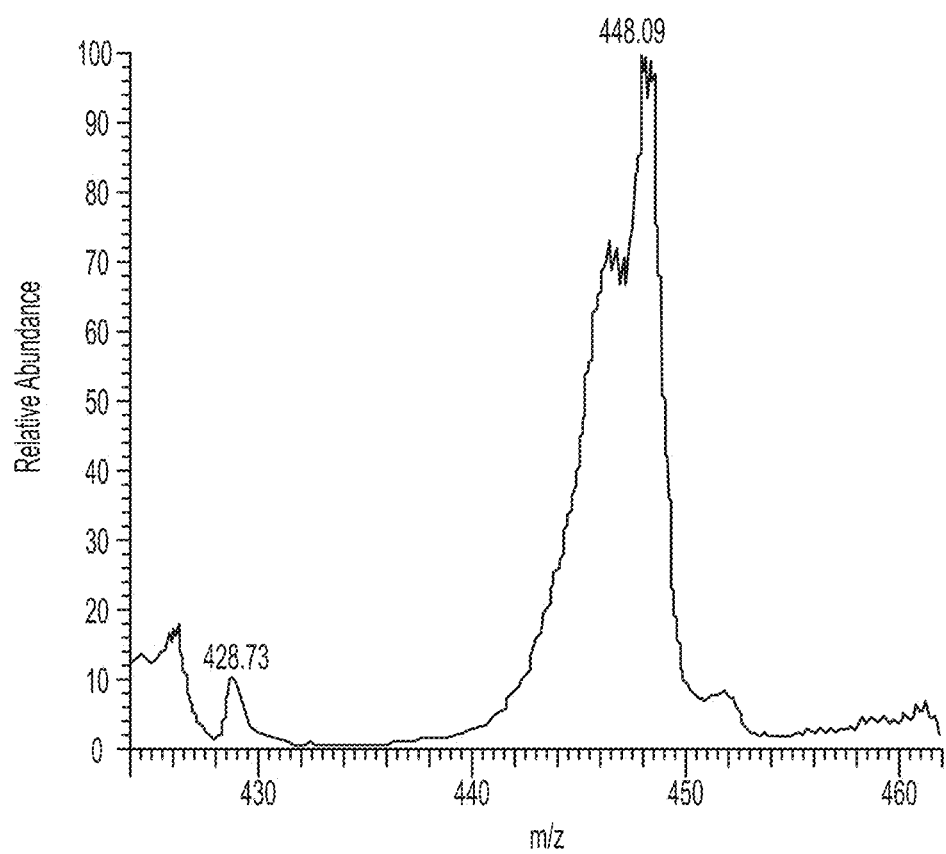
FIG. 8 depicts deuterium incorporation using dual IPTG/Tet-induced system. LTQ linear ion trap mass spectrometry data documenting extensive $^2$H incorporation in $^2$H$_2$O media without isoleucine, leucine, and valine precursor incorporation, using the dual IPTG/Tet-induced cSPP system. The tryptic fragment of the M-MLV Integrase N-terminal domain (NTD), SHSPYYM$_{(oxidation)}$LNR (SEQ ID NO: 3) (z=+3), displayed here demonstrates the efficiency of incorporation of deuterium isotope. The unlabeled peak at 428.7 mass units contributes minimally to the overall yield, and the mass distribution observed indicates species with a range of 85-100% deuterium incorporation (predicted mass for complete perdeuteration is 448.3 mass units)

Proteins were purified by a single step Ni-NTA affinity purification. The resulting isotope-enriched samples are extensively perdeuterated. FIG. 6 presents LTQ linear ion trap mass spectrometry (MS) data for representative trypsin fragments from protein samples generated using the 40-fold condensed cSPP system, with uniform $^2H$, $^{13}C$, $^{15}N$-enrichment and $^1H$—$^{13}C$ labeling of Ile($\delta1$), Leu, and Val methyl groups (referred to here as ILV-perdeuterated samples). The unlabeled peak present in each MS spectrum, 10% for CspA and 20% for EnvZB, represents a portion of the total protein with no label incorporation. This unlabeled population results from target protein expression along with MazF production, prior to culture condensation and resuspension in isotope enriched medium. While this unlabeled fraction decreases the effective yield of isotope-enriched protein, it is essentially invisible in the $^{15}N$ and/or $^{13}C$-edited NMR spectra, and its presence is not problematic for routine triple-resonance NMR studies for protein structure determination.

Where required, the fraction of unlabeled protein can be reduced using a dual control vector, in which MazF is under the control of the IPTG-inducible lac operator and the target protein is under the control of the anhydrotetracycline-induced tet operator (tetO$_1$). In this system, MazF is induced prior to condensation and, only after they are in a quasi-dormant state, the cells are condensed into isotope-enriched media, and the target protein is induced by anhydrotetracycline. This results in much lower amounts (<3%) of unlabeled target protein (see FIG. 7). The percent of overall isotope incorporated into the CspA and EnvZB proteins (i.e. in the isotope-enriched fractions indicated in FIGS. 6 and 7) is ~85% using either the IPTG or dual IPTG/Tet inducible systems. In the absence of protonated precursors for isoleucine, leucine, and valine, $^2H$ incorporation also ranges from 85-100% (FIG. 8).

Figure 9A:
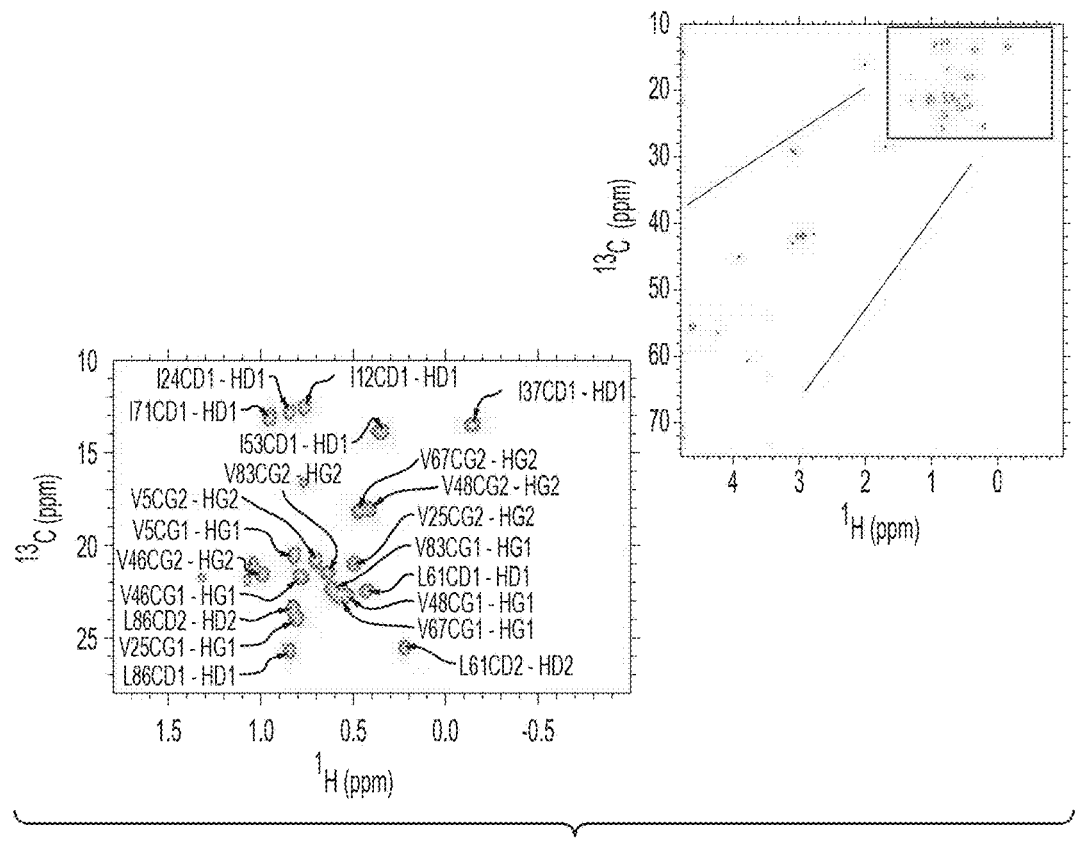
FIGS. 9A and 9 B depict [$^{13}$C—$^1$H]-HSQC spectra of $^1$H-IL(δ1)V, $^2$H, $^{13}$C, $^{15}$N-enriched (a) CspA and (b) EnvZB produced with the IPTG induced system. Peaks are present in the region of the spectrum where methyl signals appear, but little or no $^1$H—$^{13}$C signal is detected for the rest of the protein. This method does not detect the fraction of protein molecules (~10%) with $^1$H—$^{12}$C isotopic composition. Inset: Expanded methyl region of (a), with sequence-specific resonance assignments.
Figure 9B:
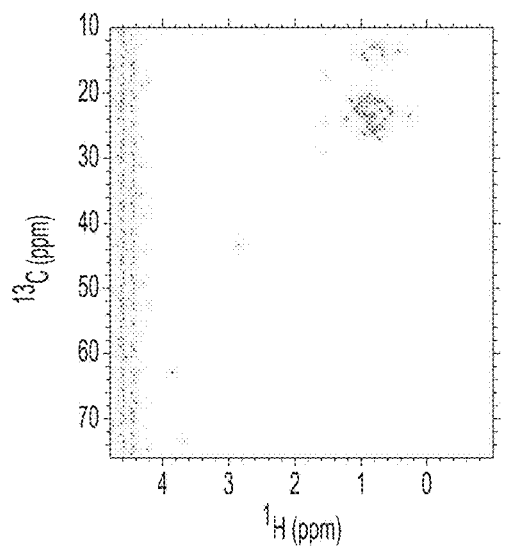

The quality of the [$^1H$—$^{13}C$]-I($\delta1$)LV, $_{13}C$, $^{15}N$, $^2H$-enriched proteins produced with the IPTG system were further assessed by 2D [$^1H$—$^{13}C$] HSQC NMR analysis (FIG. 9). These data demonstrate the expected $^{13}C$—$^1H$ peaks of the Ile($\delta1$), Leu, and Val methyl groups in the upfield region of the spectrum, and little or no resonance peak intensity in other regions of the spectrum, demonstrating that these highly-perdeuterated protein samples are suitable for triple-resonance NMR studies. Similar results are obtained using CspA produced with the dual control IPTG/tet induced system.

Figure 10:
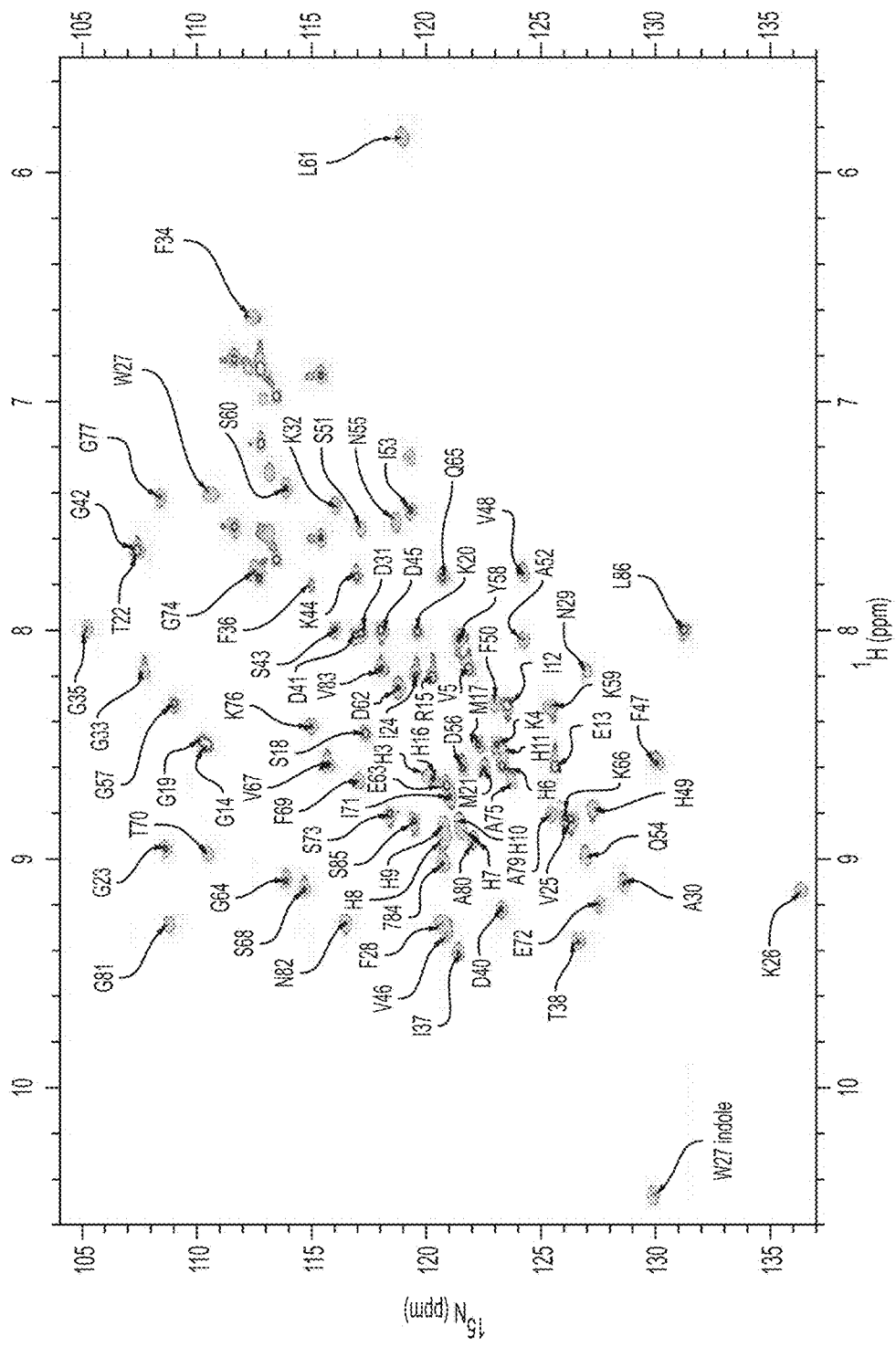
FIG. 10 depicts [$^{15}$N—$^1$H$^N$]-HSQC spectrum of CspA. Spectrum collected at pH 6.0 and 20° C. of sample of [$^1$H—$^{13}$C]—I(δ1)LV, $^{13}$C, $^{15}$N, $^2$H-enriched CspA, produced with the IPTG-induced system, and recorded on an 800 MHz NMR spectrometer. Assigned backbone H$^N$ resonances are labeled by one-letter amino acid code followed by their sequence numbers.
Figure 11:
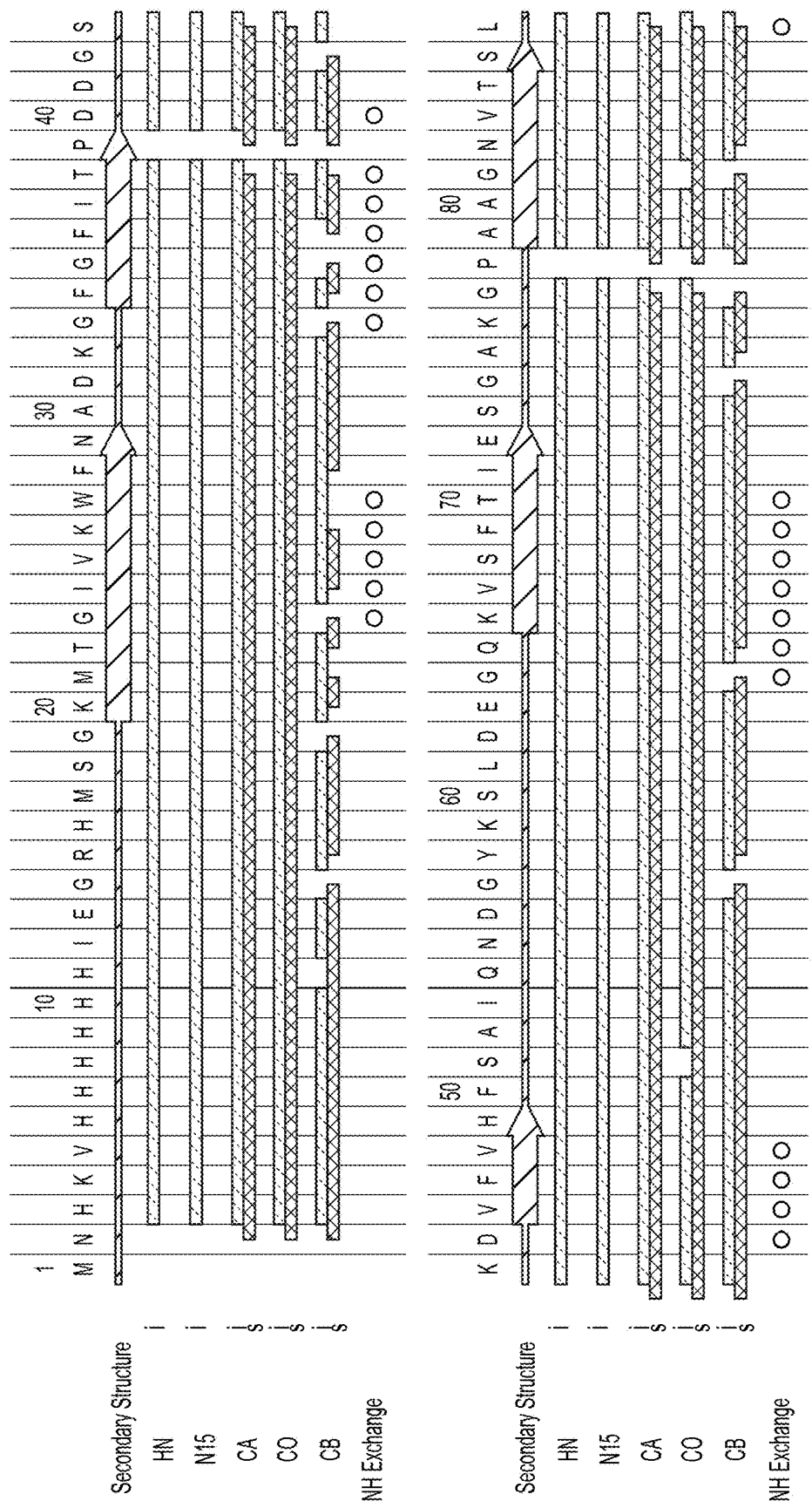
FIG. 11 depicts summary of backbone and $^{13}$C$^β$ resonances assignments for CspA derived from triple resonance NMR experiments. Red bars and yellow bars underneath the amino acid sequence represent the connectivity established between intra and sequential residues respectively. These data were obtained by analyzing six 2D and 3D NMR spectra, summarized in Table S1. Slowly exchanging backbone amides, used in the conventional structure analysis but not in the CS-Rosetta analysis, identified by $^1$H/$^2$H exchange measurements, are represented by filled circles. Secondary structures of the β-barrel found in the final structure are indicated by arrows along the amino acid sequence.

As an example of the utility of inexpensive production of perdeuterated proteins using the cSPP system, the use of these samples for rapid determination of the 3D structure of an 86-residue construct of *E. coli* CspA was evaluated. A 0.2 mM sample of ILV-perdeuterated CspA (produced with the IPTG system) was used for collection of deuterium-decoupled triple resonance experiments, including HNCO, HN(ca)CO, HNCA, HN(co)CA, HNCACB, and HN(co)CACB experiments (Table 2), collected over a period of 3.5 days at 800 MHz. FIG. 10 shows the excellent quality of the resulting 2D [$^1H^N$—$^{15}N$]-HSQC spectrum. The program AutoAssign was then used for automatic analysis of backbone $H^N$, $^{15}N$, $^{13}C^a$, $^{13}C'$, and sidechain $^{13}C^\beta$ resonance assignments, as documented in FIG. 11. The resulting resonance assignments are consistent with the published assignments for CspA (BMRB accession number 4296). Perdeuterated protein samples produced with the cSPP system thus provide high-quality NMR spectra suitable for rapid automated analysis of backbone resonance assignments.

Figure 12A:
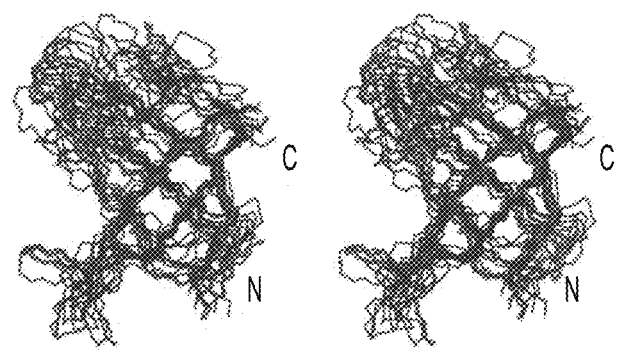
FIGS. 12A, 12B and 12C depict a stereo-view of the superimposition of Auto Structure-CNS structure for [$^1$H—$^{13}$C]—I(δ1)LV, $^{13}$C, $^{15}$N, $^2$H-enriched CspA determined by conventional automated analysis methods (blue) with the 2.0 Å X-ray crystal structure of CspA (red) (pdb ID: 1mjc). (a) Backbone line representations of the 10 lowest energy conformers obtained from AutoStructure-CNS structure compared with X-ray crystal structure. (b) Ribbon diagram of the lowest energy conformer of AutoStructure-CNS structure versus X-ray crystal structure. (c) The packing of the hydrophobic residues (viz., V9, I21, V30, V32, I37, L45, V51, F53, A64, and V67) for the lowest energy conformer of Auto Structure-CNS structure versus X-ray crystal structure.
Figure 12B:
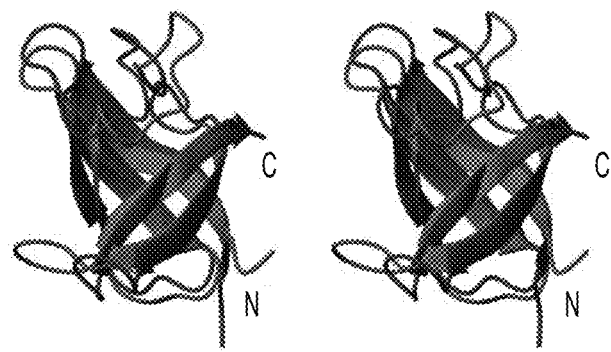
Figure 12C:
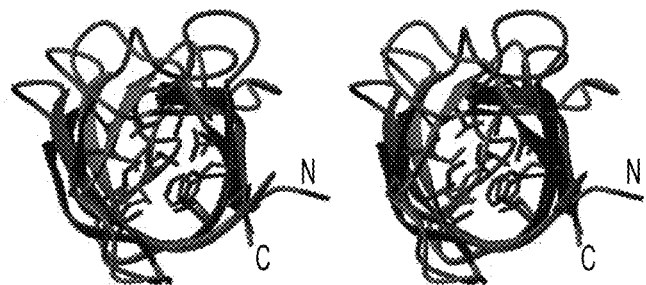

As a further example of the utility of perdeuterated samples produced with the cSPP system, rapid analysis of the 3D structure of [$^1H$—$^{13}C$]—I($\delta1$)LV, $^{13}C$, $^{15}N$, $^2H$-enriched CspA without the need for sidechain resonance assignments was also demonstrated. The use of such ILV-perdeuterated samples for fully automated analysis of small protein folds using sparse NOESY data has been previously advocated. However, the recently introduced CS-Rosetta method provides an alternative approach for small protein structure analysis using only backbone and $^{13}C^{\beta}$ chemical shift data. CS-Rosetta calculations were carried out using these resonance assignments determined with the perdeuterated CspA sample. The resulting ensemble of 10 structures, shown in FIG. 8, exhibits good structure quality scores (Table 3), and is in excellent agreement with the X-ray crystal structure of CspA, with backbone rmsd of 0.5 Å and all atom rmsd of 1.2 Å to the crystal structure for well-defined regions of the CS-Rosetta structure (1.1 Å rmsd to crystal structure for core, non-solvent-exposed sidechain atoms). In order to further assess the value of using CS-Rosetta to obtain an accurate structure of a perdeuterated protein, additional 3D $^{15}$N-edited NOESY and 3D $^{13}$C-edited NOESY data were acquired and used to assign side-chain methyl resonances, so as to determine the 3D structure by conventional automated methods with energy refinement. The resulting NMR ensemble (FIG. 12) is similar to the CS-Rosetta structure, but has lower precision, lower structure quality scores, and is less similar to the crystal structure (Table 3). Comparison of the CS-Rosetta structure with the resulting NOESY constraint list (also summarized in statistics of Table 3, reveals that essentially all subsequently-derived NOE-based distance constraints are satisfied by each of the 10 CS-Rosetta structures, cross-validating the high accuracy of the CS-Rosetta structure. These results demonstrate a cost-effective approach for rapidly determining high-quality small protein NMR structures with accuracies rivaling structures determined using more extensive NMR methods with full side-chain assignments; however, nothing substitutes obtaining a complete data set to get the most accurate structures.

Figure 13:
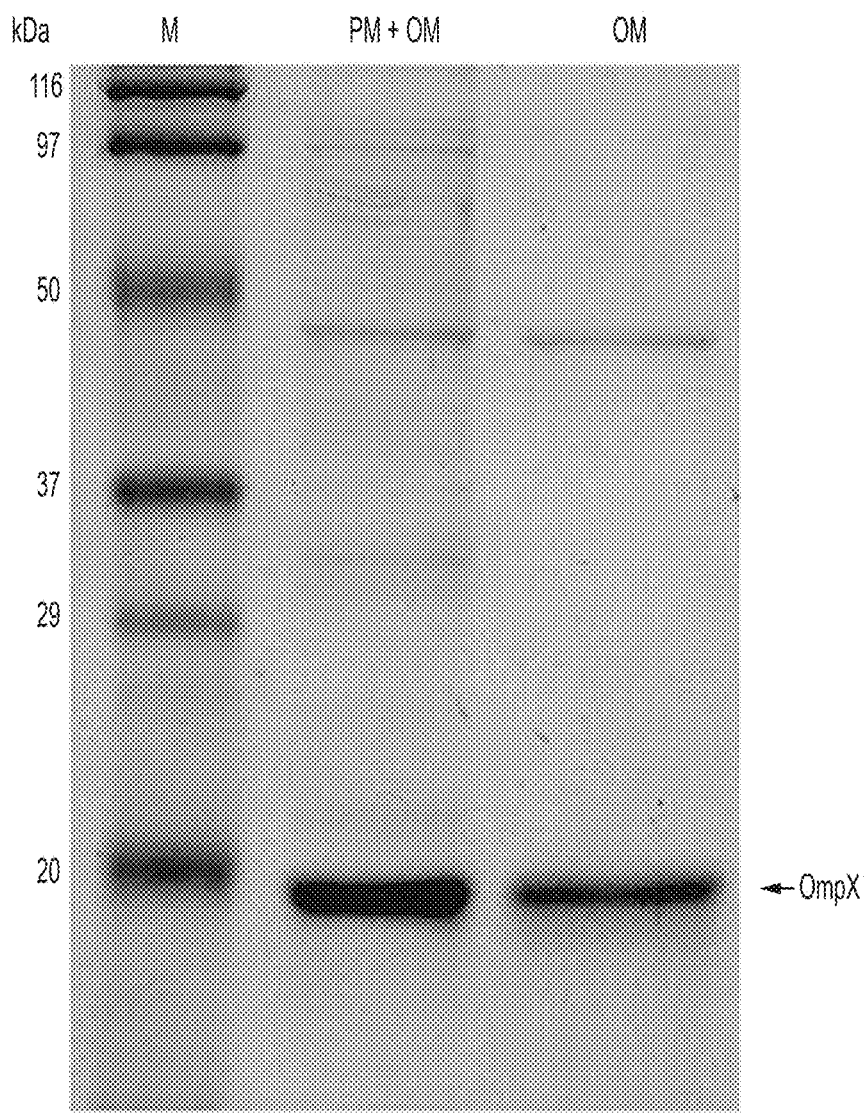
FIG. 13 depicts SDS-PAGE analysis of OmpX preparations. OmpX was expressed from pColdIV(SP4) containing the ACA-less OmpX gene along with MazF from pACYC-mazF as described above. Lane M: molecular weight marker. PM+OM: whole membrane fraction including plasma membrane and outer membrane; OM: outer membrane fraction, which was used to collect the NMR spectrum shown in FIG. 3b. The position of OmpX is indicated by an arrowhead.

Perdeutcration is essential for solution NMR studies of membrane proteins, and can be achieved at a fraction of the cost of conventional methods by using the cSPP system. As a second example of the utility of the cSPP system for cost-effective production of larger perdeuterated proteins, the production of perdeuterated membrane proteins, including the 8 kDa, 70-residue *E. coli* plasma membrane protein YaiZ, and the 16 kDa, 148-residue *E. coli* protein OmpX outer membrane protein, have also been demonstrated. The NMR sample of YaiZ was expressed using 20× condensation and OmpX was expressed using 40× condensation in per-deuterated media. Both YaiZ and OrnpX were expressed at high levels (FIG. 5). YaiZ was found exclusively in the inner membrane fraction, but not in the outer membrane fraction and inclusion bodies. An NMR sample of YaiZ was prepared by detergent extraction directly from membrane fractions using 10% 1-olcoyl-2-hydroxy-sn-glycero-3-[phospho-RAC-(1-glycerol)] (LOPG). OmpX assembles into the outer membrane (FIG. 13), rather than as inclusion bodies as typically observed for outer membrane proteins. An NMR sample of OmpX sample was prepared by solubilizing the plasma membrane fraction with 0.5% sodium lauryl sarcosinate (Sarkosyl)[20], separating the insoluble outer membrane fraction, and then extracting OmpX into 5% dodecyl-phophocholine (DPC) detergent.

Figure 15A:
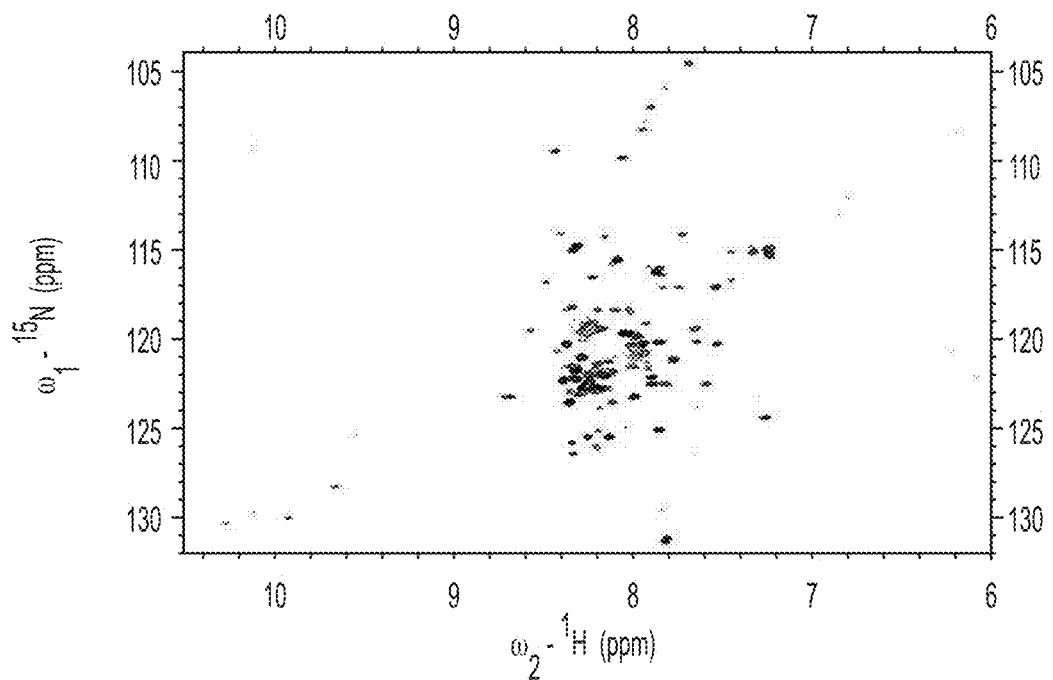
FIGS. 15A and 15B depict NMR spectra of *E. coli* membrane proteins YaiZ and OmpX. (a) 800 MHz TROSY-[H$^N$—$^{15}$N]-HSQC NMR spectrum of uniformly $^2$H, $^{13}$C, $^{15}$N-enriched YaiZ obtained at 40° C. following simple detergent extraction. (b) 600 MHz TROSY-[H$^N$—$^{15}$N]-HSQC NMR spectrum at 50° C. of uniformly $^2$H, $^{13}$C, $^{15}$N-enriched OmpX following simple detergent extraction. Target proteins (YaiZ or OmpX) were selectively isotope-enriched and perdeuterated using the cSPP system. The NMR sample of YaiZ was prepared by simple detergent solubilization of the inner membrane fraction by 25 mM MES buffer, pH 6.0, containing 10% LOPG in 95% H$_2$O/5% $^2$H$_2$O. The NMR sample of OmpX by simple detergent extraction of the outer membrane fraction by 20 mM potassium phosphate buffer, pH 6.4, containing 5% DPC in 95% H$_2$O/5% $^2$H$_2$O.
Figure 15B:
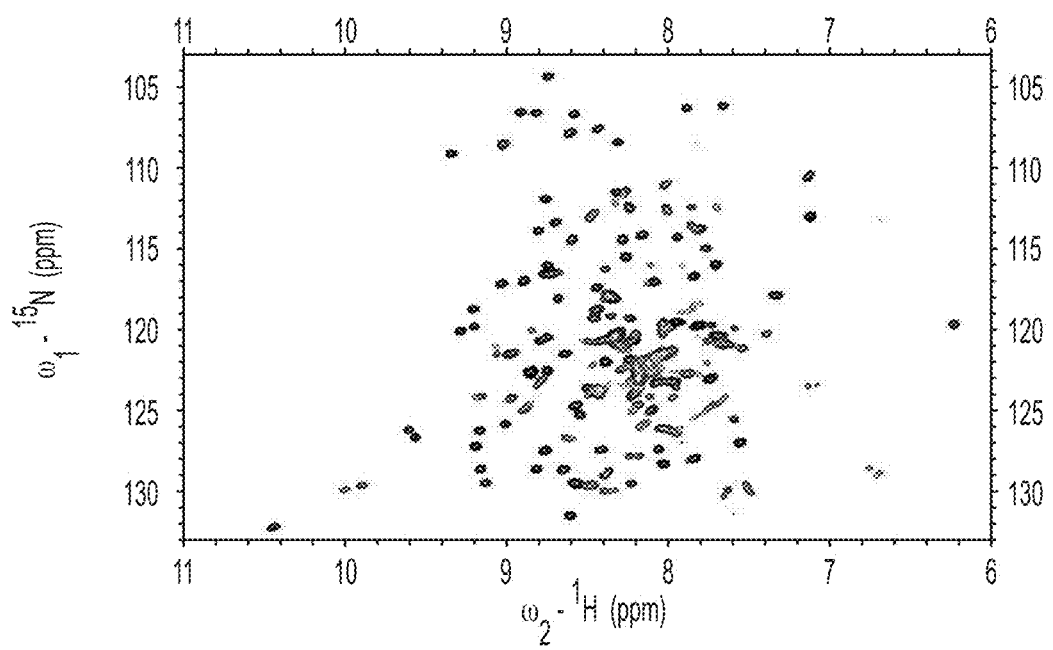

These $^{2}H$, $^{13}C$, $^{15}$N-enriched YaiZ and OmpX samples in simple detergent extracts were studied using [$H^N$, $^{15}$N] TROSY NMR at 800 and 600 MHz, respectively (FIGS. 15a and b). The YaiZ and OmpX spectra exhibit essentially of the amide peaks expected. The distribution of amide peaks in the OmpX spectrum is similar, but not identical, to that reported for reconstituted OmpX samples[19]. While further purification does improve the spectra, these samples of YaiZ in a plasma membrane detergent extract and OmpX in an outer membrane detergent extract are suitable for some structural and functional studies by NMR without any further purification; however further purification of these $^{2}$H-enriched samples would be recommended for extensive NMR structural studies or crystallization. These results demonstrate the utility of the cSPP system for production of perdeuterated membrane proteins.

DISCUSSION

These results demonstrate an important new technology for producing perdeuterated proteins for NMR and other biophysical studies. The cSPP system can be used to produce perdeuterated, $^{13}$C, $^{15}$N-enriched protein samples, with methyl, aromatic, or other $^{1}$H—$^{13}$C labeling patterns, as required, at a fraction of the cost of conventional systems with similar protein production yields. These methods have applications for studies of larger proteins, protein-protein complexes, and membrane proteins.

The most important feature of the SPP method is that cells are no longer growing following MazF induction. Therefore, the only protein being produced in the "semi-dormant state" is the target protein—i.e. all of the $^{13}$C, $^{15}$N isotope is incorporated into the target protein, and none into other proteins, providing the ability to selectively detect the target protein using $^{13}$C and/or $^{15}$N-edited NMR experiments. Using conventional methods, these isotopes would be incorporated into many different proteins—i.e. the labeling would not be selective to the targeted protein. In addition, in the quiescent state the cells are dormant, with minimal recycling of unlabeled amino acids into new protein synthesis. The cSPP method can also be used in some cases to condense cells to very high densities (e.g. 40× or higher) in isotope-enriched media with no significant reduction in protein production yields per cell. Thus, the cSPP method has significant advantages over simply resuspending cells at higher concentrations in labeled media.

Routine access to inexpensive perdeuterati on methods also provides a route to fully automated analysis of backbone assignments and 3D structures of smaller (<12 kDa) proteins. The studies discussed herein demonstrate cost-effective production of $^{2}$H, $^{13}$C, $^{15}$N-enriched proteins in the cSPP system. The resulting sample of CspA, purified with a single-step Ni-NTA affinity chromatography, allowed data collection and automated analysis of backbone $^{1}H^N$, $^{15}$N, $^{13}C^{\alpha}$, $^{13}$C', as well as sidechain $^{13}C^{\beta}$, assignments in only a few days. These data for a perdeuterated protein provided high-quality 3D structures of CspA using CS-Rosetta, rivaling the best NMR structures available to date for CspA using conventional methods requiring essentially complete sidechain proton assignments. Sparse NOESY data (e.g. $H^N$—$H^N$ or $H^N$—$CH_3$ NOEs) can also be used, as necessary, to refine the CS-Rosetta structure. This represents a general approach to rapid structure analysis of small (<150 residue) proteins. This approach has tremendous value in generating assignments and structural information for small molecule screening studies, as well as in high-throughput structural and functional genomics studies.

In the case of membrane proteins, the selective labeling provided by the single protein production system allows NMR studies of a targeted membrane protein following simple detergent extraction. NMR spectra can be obtained without extensive purification or reconstitution, allowing a membrane protein's structural and functional properties to be characterized prior to reconstitution, or as a probe of the effects of subsequent purification steps on the structural integrity of membrane proteins.

In conclusion, the condensed-phase SPP technology for protein production allows cost-effective production of milligram quantities of perdeuterated proteins, facilitating many NMR, neutron diffraction, and other biophysical applications. The current technology typically provides samples that are ~85% enriched in $^2$H, and 100% enriched in $^{15}$N and $^{13}$C. As demonstrated here for CspA, this labeling is sufficient for rapid analysis of resonance assignments and 3D structures of small soluble proteins and for production of valuable perdeuterated samples of larger soluble proteins and membrane proteins. The 10-40 fold reduction in costs of perdeuterated fermentation media provided by using the cSPP system opens the door to many new applications for perdeuterated proteins in spectroscopic and crystallographic studies.

What is claimed:

1. A vector system comprising:
a two plasmid protein production system comprising:
a first plasmid comprising
   (a) a Tn10 promoter-operator region comprising a mutated tetA promoter adjacent to a cspA cold shock promoter,
   (b) a tetR repressor gene under the control of the Tn10 promoter-operator region,
   (c) a tetO operator, and
   (d) a target gene under the control of the cspA promoter and the tetO operator, and
a second plasmid comprising
   (e) a lac operator, and
   (f) a gene encoding MazF under the control of the lac operator,
   wherein the target gene on the first plasmid encodes an mRNA sequence that is not recognized by MazF, wherein the RNA recognition sequence of MazF is -ACA-, and
   wherein expression of the target gene is induced after induction of expression of the gene encoding MazF are such that the target protein is isotope-enriched.

2. The vector system of claim 1, wherein the first plasmid further comprises a nucleic acid sequence encoding an outer membrane protein A (OmpA) signal peptide.

3. The vector system of claim 1, wherein the target gene encoding the target protein is sub-cloned into the first plasmid between a first restriction site and a second restriction site.

4. The vector system of claim 1, wherein the first plasmid further comprises nucleic acid sequences derived from a cspA gene that flank the target gene.

5. The vector system of claim 1, wherein expression of the target gene is induced by tetracycline or a tetracycline analog.

6. The vector system of claim 5, wherein the tetracycline analog is anhydrotetracycline.

7. The vector system of claim 1, wherein the target protein is 70-100% isotope-enriched.

* * * * *